US008270561B2

(12) United States Patent
Zamyatin et al.

(10) Patent No.: US 8,270,561 B2
(45) Date of Patent: Sep. 18, 2012

(54) MOTION WEIGHTING IN COMPUTED TOMOGRAPHY (CT) WITH CONE ANGLE

(75) Inventors: Alexander Zamyatin, Hawthorn Woods, IL (US); Be-Shan Chiang, Buffalo Grove, IL (US); Satoru Nakanishi, Tochigi-ken (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 0 days.

(21) Appl. No.: 12/903,508

(22) Filed: Oct. 13, 2010

(65) Prior Publication Data

US 2012/0093281 A1  Apr. 19, 2012

(51) Int. Cl.
*A61B 6/00* (2006.01)
(52) U.S. Cl. .................................. 378/8; 378/4; 378/15
(58) Field of Classification Search .................. 378/4, 8, 378/15
See application file for complete search history.

(56) References Cited

U.S. PATENT DOCUMENTS

| | | | |
|---|---|---|---|
| 5,991,356 A * | 11/1999 | Horiuchi et al. | 378/8 |
| 6,327,326 B1 * | 12/2001 | Flohr et al. | 378/8 |
| 6,421,552 B1 * | 7/2002 | Hsieh | 600/425 |
| 6,925,141 B2 * | 8/2005 | Bruder et al. | 378/8 |
| 7,020,234 B2 * | 3/2006 | Bruder et al. | 378/8 |
| 7,889,901 B2 * | 2/2011 | Bontus et al. | 382/128 |
| 2007/0140535 A1 * | 6/2007 | Li et al. | 382/128 |
| 2007/0195925 A1 * | 8/2007 | Shechter et al. | 378/17 |
| 2008/0273778 A1 * | 11/2008 | Goto et al. | 382/131 |
| 2009/0154639 A1 | 6/2009 | Nakanishi et al. | |

OTHER PUBLICATIONS

Zamyatin et al., Reconstruction Algorithm for Wide Cone Beam Helical CT, IEEE Nuclear Science Symposium Conference Record, 2005, pp. 2278-2282.*
Manzke et al., Helical cardiac cone beam CT reconstruction with large area detectors: a simulation study, Phys Med Biol, 50, 2005, pp. 1547-1568.*
U. van Stevendaal et al, A motion-compensated scheme for helical cone-beam reconstruction in cardiac CT angiography, Med Phys, 35 (7), 2008, pp. 3239-3251.*
Zamyatin et al., Helical CT Reconstruction with Large Cone Angle, IEEE Nuclear Science Symposium Conference Record, 2006, pp. 2264-2267.*
Grass et al., Helical cardiac cone beam reconstruction using retrospective ECG gating, Phys Med Biol, 48, 2003, pp. 3069-3084.*
Zamyatin et al., Motion weighting in helical computed tomography with wide cone angle, IEEE, 2010, pp. 2860-2863.*
Koken, P and Grass, M., "Aperture weighted cardiac reconstruction for cone-beam CT", Phys Med Biol., 51, pp. 3433-3448 (2006).
Noo, Frederic et al., "Image reconstruction from fan-beam projections on less than a short scan", Phys Med Biol., 47, pp. 2525-2546 (2002).

* cited by examiner

*Primary Examiner* — Alexander H Taningco
(74) *Attorney, Agent, or Firm* — Knoble Yoshida & Dunleavy, LLC

(57) ABSTRACT

Embodiments and processes of computer tomography perform tasks associated with weighting projection data based upon at least one motion index such as electrocardiogram gated reconstruction, view-based motion map and ray-based motion map. Other embodiments and processes of computer tomography perform tasks associated with weighting projection data based upon at least one motion index and another index that is associated with certain geometric characteristics of a cone beam.

40 Claims, 11 Drawing Sheets

MMAP IS NORMALIZED BY USING maxMmap AND minMmap

MOTION WEIGHTING IN COMPUTED TOMOGRAPHY (CT) WITH CONE ANGLE

This application is partially related to Patent Application Publication 2009/0154639 published on Jun. 18, 2009A1, Nakanishi et al.

FIELD

Embodiments described herein generally relate to motion weighting in CT imaging systems and methods.

BACKGROUND

As a number of detector rows increases, the increasing cone angle has become an important factor in a practical reconstruction algorithm. In this regard, prior art technologies have embraced an exact helical cone beam algorithm of the shift invariant FBP type (Katsevich algorithm), which use only data within the helical PI-intervals. In other words, data are used only within the N-PI window, where N=1, 3, . . . , is the number of helical half-turns.

The N-PI window weighting has the following disadvantages. Since some measured data located outside the N-PI window is not used, extra X-ray dose is unnecessarily imposed on the patient. In addition, because all data within the N-PI window is used with the same weight, an algorithm generally becomes more sensitive to patient motion and imperfections of real data despite the noise reduction. Lastly, the N-PI reconstruction limits the helical pitch. For example, pitches in the range of 0.75-0.85 are too fast to be used with the 3-PI window and are suboptimal to use with the 1-PI window since only a small fraction of data is utilized.

Meanwhile, 2D fan beam redundancy weighting has advantages such as easy adjustment to the helical pitch and smooth transition from 0 to 1. That is, an algorithm is more stable to patient motion and imperfections of real data. On the other hand, when motion is present, exactness needs to be balanced with stability to motion. Prior art approaches generally disregard increasing cone angle and are not suitable for fully 3D reconstruction.

DETAILED DESCRIPTION

Figure 1:
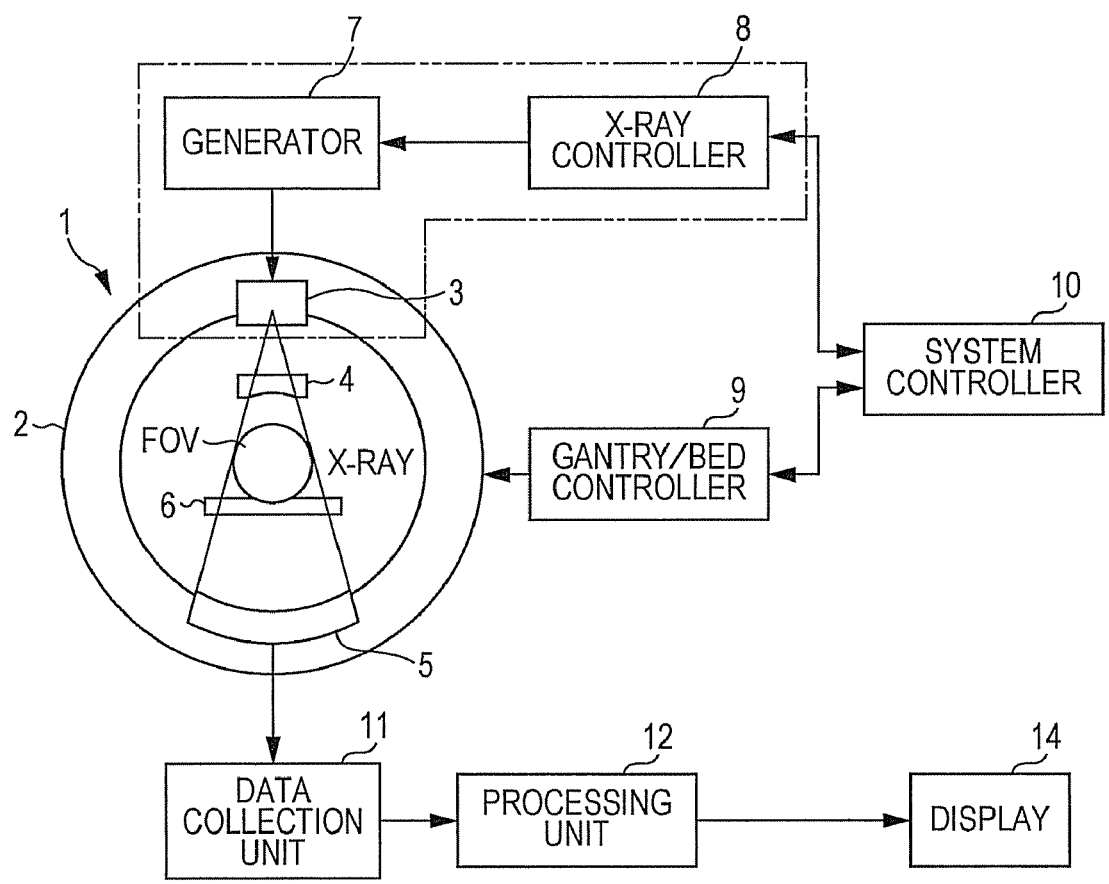
FIG. 1 is a diagram illustrating an x-ray computed topographic imaging system according to the present invention.

FIG. 1 is a diagram illustrating an x-ray computed topographic imaging system according to the present invention. The projection data measurement system includes a gantry 1, which accommodates an x-ray source 3 and a two-dimensional array type x-ray detector 5. An x-ray source 3 and two-dimensional array type x-ray detector 5 are installed on a rotating ring 2 in facing opposite sides of a subject, who is laid on a sliding sheet of a bed 6. The rotating ring 2 rotates around a predetermined rotational axis while the sliding bed 6 moves along the rotational axis at a predetermined speed. A gantry/bed controller 9 synchronously controls the revolution of the rotating ring 2 and the sliding movement of the sliding bed 6. In the following embodiments, projection data is collected while the x-ray source 3 travels either a helical path in a helical scanning system or a circular path in a circular scanning system.

The x-ray source 3 emits a cone-beam or approximately cone-shaped x-ray flux that is directed onto the subject through an x-ray filter 4. An x-ray controller 8 supplies a trigger signal to a high voltage generator 7, which applies high voltage to the x-ray source 3 upon receiving the trigger signal. Furthermore, a system controller 10 exerts an overall control over both the x-ray controller 8 and the gantry/bed controller 9 so that x-rays are emitted continuously or intermittently at fixed angular intervals from the x-ray source 3 while the rotating ring 2 and the sliding bed 6 are respectively in predetermined rotation and motion.

X-rays that have passed through the subject are detected as electrical signals by the two-dimensional array type x-ray detector 5. In the x-ray detector 5, a plurality of detector elements are arranged in one dimensional row, and a plurality of the rows is stacked to construct a two-dimensional array. In certain situation, each detector element corresponds with one channel. A data collection unit 11 amplifies the output signal from the two-dimensional array type x-ray detector 5 for each channel and converts to a digital signal so as to produce projection data.

A processing unit 12 subsequently performs various processing tasks upon the projection data that has been delivered from the data collection unit 11. For example, the processing unit 12 performs on the projection data desired operation including but not limited to data sampling and shifting, filtering, backprojection and reconstruction. The processing unit 12 determines backprojection data reflecting the x-ray absorption in each voxel. In a circular scanning system using a cone-beam of x-rays, the imaging region (effective field of view) is of cylindrical shape of radius R centered on the axis of revolution. The processing unit 12 defines a plurality of voxels (three-dimensional pixels) in this imaging region and finds the backprojection data for each voxel. The three-dimensional image data or tomographic image data is compiled based upon the backprojection data, and a display device 14 displays a three-dimensional image or tomographic image according to the three-dimensional image data.

As will be later described, the processing unit 12 also performs tasks related to weighting on the projection data before backprojection and reconstruction. In certain embodiments, the processing unit 12 performs weighting on the projection data according to motion before backprojection and reconstruction. The motion weighting is an important task for improving an image of non-stationary organs such as the heart and lungs according to the current invention. Furthermore, in other embodiments, the processing unit 12 optionally performs weighting on the projection data according to a combination of motion and cone beam characteristics before backprojection and reconstruction.

As well known, an object or patient attenuates the x-ray photon beam (ray), and the attenuated intensity I at the detector element k is defined in Equation (1) as follows:

$$I_k = I_k^0 \exp(-\int_l \mu(x) dx) \quad (1)$$

where $\mu(x)$ is the attenuation function to be reconstructed, $I_k^0$ the beam intensity before attenuation by $\mu(x)$ as originally produced by the x-ray tube but after penetrating through the x-ray (wedge, bowtie) filter, and $\int_l \mu(x) dx$ is the line integral of $\mu(x)$ along the line l. Mathematically, $\mu(x)$ can be reconstructed given a set of line integrals corresponding to a plurality of the lines l. Therefore, measured intensity data are to be converted into line integrals as follows in Equation (2):

$$\int_l \mu(x) dx = \ln(I_k^0) - \ln(I_k) \quad (2)$$

X-ray tomographic reconstruction consists of the following three main steps, data acquisition, data processing and data reconstruction. In data acquisition, the x-ray intensity data are collected at each detector element of the detector 5 and at each predefined angular view position β while the gantry 1 is rotated. The detector 5 measures incident x-ray flux by integrating energy (charge) or counting photons, and the measured signal is converted into an electric signal. Then, the electric signal is transferred from a rotating part of the gantry 1 to a stationary part though the slip ring 2.

In data processing, data is converted from x-ray intensity measurements to the signal corresponding to line integrals according to Equation (2). Also, various corrections steps are applied to reduce effects of undesired physical phenomena such as scatter, x-ray beam hardening, compensate non-uniform response function of each detector element, and to reduce noise.

Depending on the algorithm, data reconstruction contains all or some of the following processing steps. For example, cosine weighting is performed with respect to fan angle and or cone angle and is defined as x cos or 1/cos. A second exemplary step is data differentiation with respect to any combination of fan angle, cone angle, projection angle, source trajectory coordinate, vertical detector coordinate and horizontal detector coordinate. A third exemplary step is data redundancy weighting to multiply data by a weight function W, which is a function of any combination of fan angle, cone angle, projection angle, source trajectory coordinate, vertical detector coordinate and horizontal detector coordinate. A fourth exemplary step is convolution or filtering based upon convolution kernel. Some algorithms use ramp-based kernel (H(w)=|w|), while others use Hilbert-based kernel (h(t)=1/t, h(t)=1/sin(t), H(w)=i sign(w)). Kernels are adjusted according to any combination of the fan beam geometry that are scaled, modulated, apodised, and or modified. The order in which the above steps are applied depends on a specific reconstruction algorithm.

Backprojection projects data back in the image domain. In general, backprojected data is weighted by a distance factor. The distance factor is inversely proportional to the distance L from the x-ray source position to the reconstructed pixel. The distance factor can be proportional to $1/L$ or $1/L^2$. Also, some additional data redundancy weighting is optionally applied during the backprojection step on the pixel-by-pixel basis. The backprojection step generally obtains data value corresponding to the ray through the reconstructed pixel by either data interpolation or data extrapolation. This process can be done in a numerous variety of ways.

In the present invention, the processing unit 12 of FIG. 1 performs data redundancy weighting in various manners as illustrated in the following embodiments. In some embodiments or processes, weighting is related to motion alone. In other embodiments or processes, weighting is related to a combination of motion and cone beam characteristics such as a fan angle and a cone angle. Motion is determined by certain predetermined indexes such as electrocardiogram gated reconstruction (EGR) and motion map (MMAP). These embodiments and processes are merely exemplary and are optionally implemented in a variety of different ways based upon the combinations of weighting functions that will be described below and or are found elsewhere but well known in the industry.

In a first group of embodiments, weighting is addressed primarily to motion. In clinical applications, two major types of motion include motion of the heart (cardiac motion) and lung motion. Cardiac data is generally obtained over several heart beats at a slow helical pitch so that redundant data are sufficiently available for gated reconstruction. During the data acquisition, electrocardiogram (ECG) is also obtained for information on cardiac motion.

Still in relation to the first group of embodiments for motion weighting, lung data is acquired in the following manner. In general, lung data is collected at a faster helical pitch so that some redundant data is available, but it is not usually enough for gated reconstruction. In some cases, lung data may be sufficient only for a very limited gated reconstruction. Unlike ECG for the cardiac motion, no external motion information is generally available for reconstruction with respect to lung data.

In both cardiac and lung cases, available redundant data is weighted based on object motion. The main idea is to use motion weighting so that more weight is assigned to the rays with less motion. In the following disclosure on the exemplary embodiments, a processing unit is used to generally refer to the processing unit 12 of FIG. 1 or its equivalent device, which performs tasks related to the above described weighting functions. By the same token, in the following disclosure on exemplary processes or methods, a processing step is used to generally include steps or sub steps that are related to the above described weighting functions.

In the first group of embodiments, projection data is weighted primarily based upon a single motion index, and the projection data is acquired using a cone beam source in a circular path. The first group of embodiments also optionally weights projection data based upon a combination of a single motion index and fan beam characteristics, and the projection data is acquired using a cone beam source in a circular path. The first group of embodiments further optionally weights projection data based upon a combination of multiple motion indexes and fan beam characteristics, and the projection data is acquired using a cone beam source in a circular path.

Figure 2:
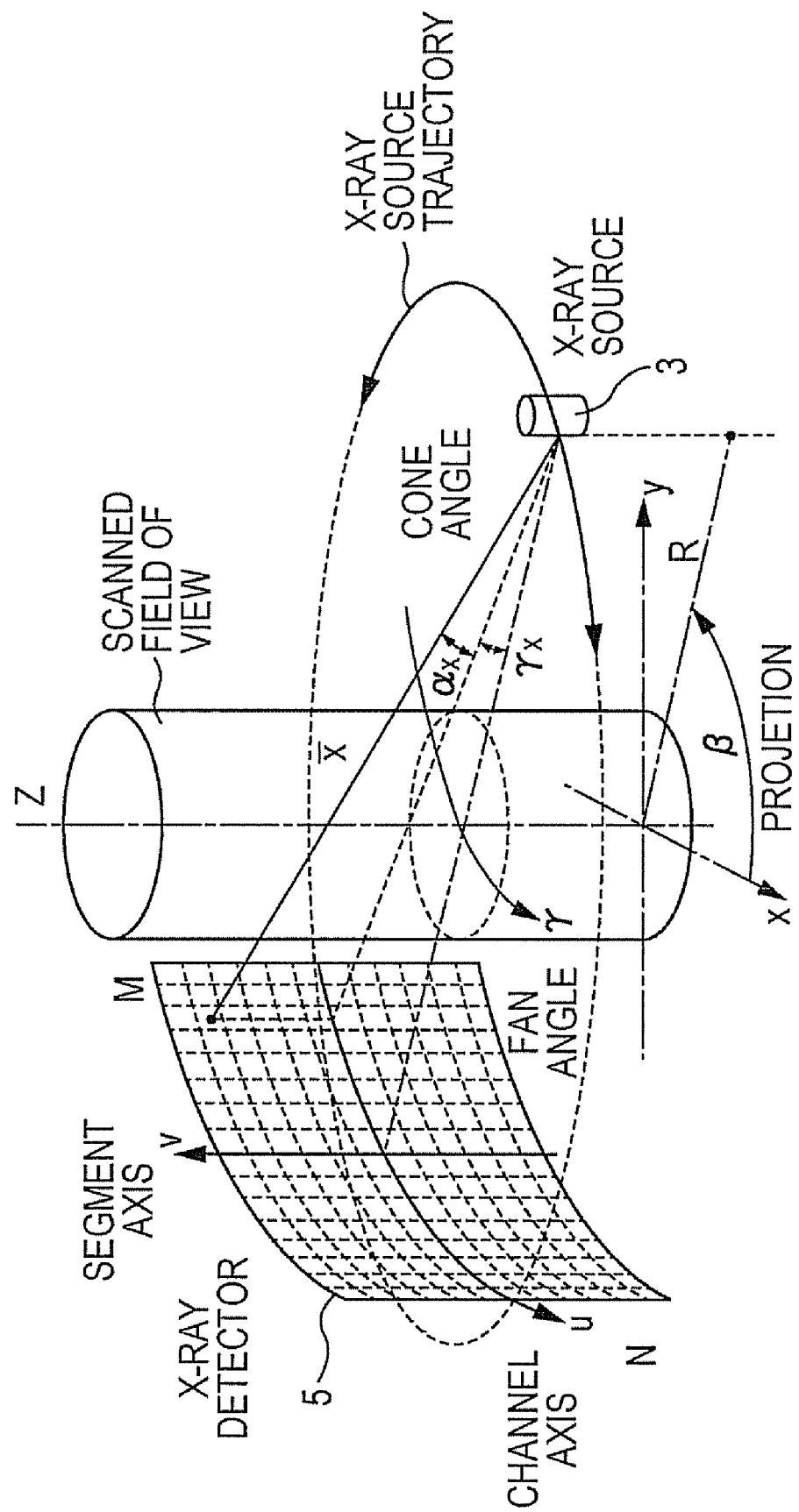
FIG. 2 is a diagram illustrating the system geometry for a cone-beam system for circular data acquisition according to the invention.

Now referring to FIG. 2, a diagram illustrates the system geometry for a cone-beam system for and a method of circular data acquisition according to the invention. In general, X-rays are emitted from the X-ray source 3 at a plurality of projection angles around the object to collect at least minimally required tomographic data. At each of a projection angle β with respect to the x axis, x-rays are emitted with a cone angle α and a fan angle γ and pass through an object with a scanned field of view. The source 3 and the two-dimensional detector 5 are diametrically positioned across the rotating axis. As the source 3 travels over a predetermined circular path, the two-dimensional detector 5 detects the x-rays. The predetermined circular trajectory of the source 3 is defined as $\lambda(\beta) = (R \cos(\beta - \beta_0), R \sin(\beta - \beta_0))$, where R is the radius of the source trajectory while $\beta_0$ is an initial projection angle. The data acquisition is optionally repeated as the object is moved along the rotational axis in a stepping manner. The two-dimensional detector 5 is described to have a detector element k from k=1 to N·M, where N is the number of detector rows while M is the number of elements per detector row.

In a first embodiment, the processing unit or step performs tasks of weighting projection data that has been acquired during a circular trajectory of a cone beam source according to the cardiac phase. The first embodiment includes both 2D and 3D cases. During the data acquisition, cardiac data are obtained so that redundant data are sufficiently available for gated reconstruction over several heart beats. In addition, electro cardiogram (ECG) is also obtained for heart motion information during the data acquisition. In general, after acquiring the projection data using a cone beam along a circular trajectory, the processing unit or step ultimately determines a weighting value according to an electrocardiogram gated reconstruction (EGR) weighting function.

The EGR weighting $w_{EGR}(\beta, \gamma)$ is function of view angle β and fan angle γ and is normalized as defined below in Equation (3).

$$w_{EGR}(\beta, \gamma) = \frac{u_{EGR}(\varphi(\beta))}{\sum_{n=-N_{PI}}^{N_{PI}} u_{EGR}(\varphi(\beta_n^C))} \quad (3)$$

In general, the normalized EGR weighting function $w_{EGR}(\beta, \gamma)$ is determined by normalizing an EGR weighting function, $u_{EGR}(\varphi(\beta))$ over a summation of $u_{EGR}(\varphi(\beta_n^C))$ from $n = -N_{PI}$ to $n = N_{PI}$ for complementary view angles $(\beta_n^C)$. One exemplary definition of the complementary view angles $(\beta_n^C)$ is defined by Equation (4):

$$\beta_n^C(\beta, \gamma) = \begin{cases} \beta + 2\gamma + n\pi, & n \text{ odd} \\ \beta + 2n\pi, & n \text{ even} \end{cases} \quad (4)$$

The value of $N_{PI}$ is determined to be as large as necessary to take into account all available cardiac data. The normalized EGR weighting function $w_{EGR}(\beta, \gamma)$ determines a weighting value ranging from 0 to 1 with respect to a particular view angle β and a particular fan angle γ.

In further detail, one example of EGR weighting function, $u_{EGR}(\varphi(\beta))$ is defined as follows in Equation (5). At a cardiac phase φ and a view angle β, an EGR weighting function $u_{EGR}(\varphi(\beta))$ is defined as:

$$u_{EGR}(\varphi(\beta)) = \exp\left(-\frac{(\varphi(\beta) - \varphi_0)^2}{\sigma_{EGR}^2}\right) \quad (5)$$

where a slice is reconstructed at a phase $\phi_0$ while $\sigma_{EGR}$ is a predetermined empirical parameter. For example, by choosing a smaller value for $\sigma_{EGR}$, since the cardiac window becomes narrower, temporal resolution increases.

Figure 3:
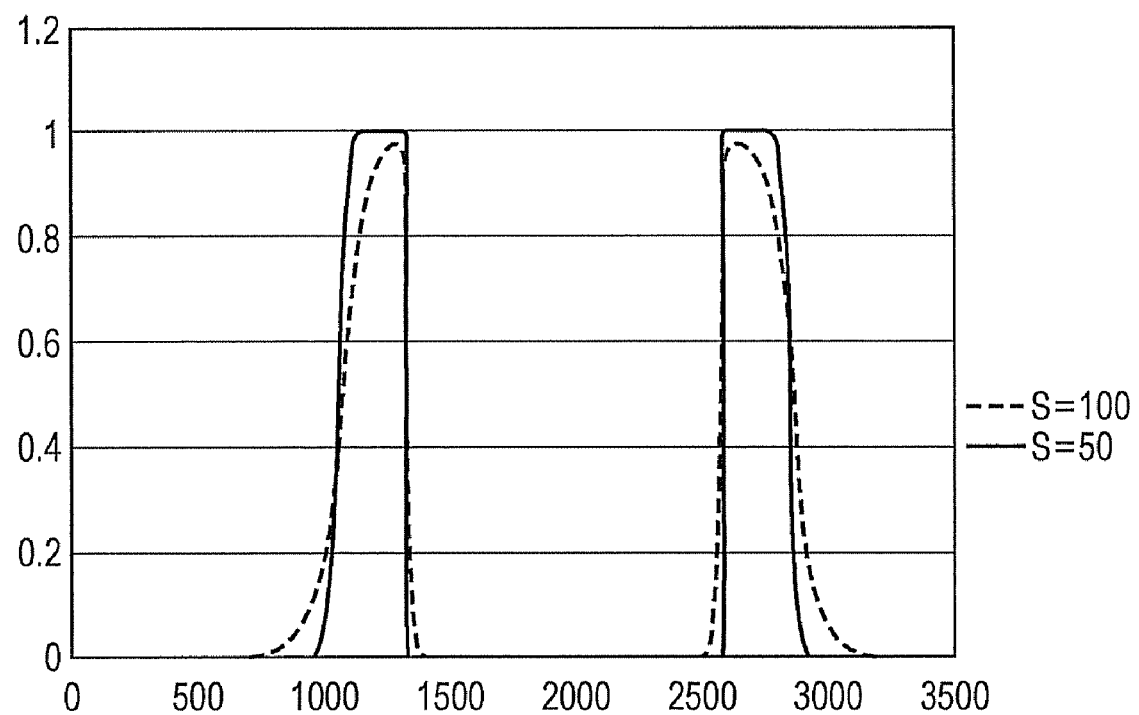
FIG. 3 illustrates an effect of the parameter, $\sigma_{EGR}$ on the weight.

Now referring to FIG. 3, the effect of the parameter, $\sigma_{EGR}$ is illustrated on the combined weight. The X axis is views while the Y axis is weight. In this example, two patches are actually used per slice. For example, the cardiac window becomes narrower as illustrated in solid lines at $\sigma_{EGR}=50$ views than that as illustrated in dotted lines at $\sigma_{EGR}=100$ views. That is, by making the $\sigma_{EGR}$ value smaller, as the cardiac window becomes narrower, temporal resolution increases.

In further detail, the parameter $\sigma_{EGR}$ is optionally decided based on another parameter, Λ, which represents a minimum backprojection range. To determine the parameter $\sigma_{EGR}$, the following iterative process is utilized according to one example:

1. Start with a small value of $\sigma_{EGR}$ and compute initial patch sizes.
2. Check if angular data patches cover Λ.
3. If not, increase $\sigma_{EGR}$ by a predetermined step size and regenerate new patch sizes.
4. Continue the iterations until patch sizes are large enough to cover Λ.

In summary, a more weight value is assigned to a view that is quieter or has less cardiac motion while a less weight value is assigned to a view that is move active or has more cardiac motion. For example, the highest weight value 1 is assigned to a view that has the least cardiac motion while the lowest weight value 0 is assigned to a view that has the most cardiac motion.

Finally, the processing unit or step performs tasks of weighting projection data according to the above determined normalized EGR weight value. That is, each of the projection data pd (β, γ, v) is weighted by the normalized EGR weight value $w_{EGR}(\beta, \gamma)$, which has been determined for a corresponding view β and a corresponding fan angle γ. The above determined weight value in effect selects the most valid views of all complementary views.

Although the above embodiment is described with respect to cardiac motion, the same concept is applicable to lung motion. Since lung data is generally collected at a faster rate than cardiac data, redundant data may not be sufficiently available for gated reconstruction or may be available for a very limited gated reconstruction. Furthermore, unlike ECG for cardiac data, no outside motion information is available for reconstruction.

In a second embodiment, the processing unit or step performs tasks of weighting projection data that has been acquired during a circular trajectory of a cone beam source according to a motion map. The second embodiment includes both 2D and 3D cases. In general, after acquiring the projection data using a cone beam along a circular trajectory, the processing unit or step ultimately determines a normalized weighting value according to a view-based motion map (vMMAP) weighting function.

The vMMAP weighting $w_{vMMAP}(\beta, \gamma)$ is function of view angle β and fan angle γ and is normalized as defined below in Equation (6).

$$w_{vMMAP}(\beta, \gamma) = \frac{u_{vMMAP}(\beta)}{\sum_{n=-N_{PI}}^{N_{PI}} u_{vMMAP}(\beta_n^C)} \quad (6)$$

In general, the normalized vMMAP weighting function $w_{vMMAP}(\beta,\gamma)$ is determined by normalizing vMMAP weighting function, $u_{vMMAP}(\beta)$ over a summation of $u_{vMMAP}(\beta_n^C)$ from $n=-N_{PI}$ to $n=N_{PI}$ for complementary view angles ($\beta_n^C$). One exemplary definition of the complementary view angles ($\beta_n^C$) is defined by Equation (4). The value of $n=N_{PI}$ is determined to be as large as necessary to take into account all available cardiac data. The normalized vMMAP weighting function $w_{vMMAP}(\beta,\gamma)$ determines a weight value ranging from 0 to 1 with respect to a particular view angle $\beta$ and a particular fan $\gamma$.

In one example, the vMMAP weighting function, $u_{vMMAP}(\beta)$ is ultimately related to a view-based motion map vMMAP as follows in Equation (7A). At a view angle $\beta$, the vMMAP motion map function is defined as:

$$vMMAP(\beta) = \sum_{ch} \text{abs}(diff[ch, \beta]) \quad (7A)$$

The motion map function vMMAP($\beta$) for a particular view is the sum of absolute difference (SAD) across channels. In each of the views, the SAD value indicates inconsistency that has been caused by motion of a non-stationary object such as the heart.

Figure 4A:
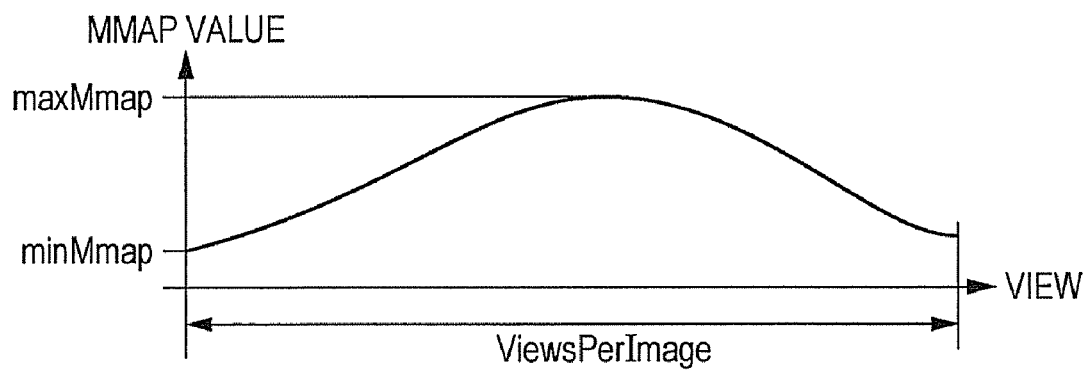
FIG. 4A is a graph illustrating an motion map.
Figure 4A:

Now referring to FIG. 4A, the motion map function vMMAP ($\beta$) generates a hypothetical graph based upon the above described sum of absolute difference (SAD) across channels. The x axis is views, and a double-headed arrow indicates a ViewPerImage that is a particular number of views or a range for each image. The y axis indicates a motion map value in an arbitrary unit. The graph illustrates exemplary motion map values with a max motion map (maxMmap) value and a minimal motion map (minMmap) value within the viewPerImage.

Figure 4B:
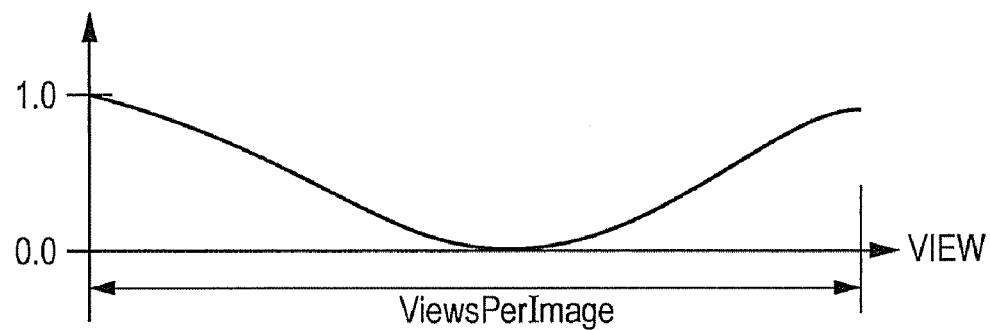
FIG. 4B is a graph illustrating a normalized motion map.

Now referring to FIG. 4B, a graph illustrates a normalized motion map. In one example, a max motion map (maxMmap) value and a minimal motion map (minMmap) value are found for all views within a reconstruction view range. That is, the minMmap function and the maxMmap function are defined as follows:
maxMmap=max(MMAP($\beta$)) for all $\beta$'s in a reconstruction view range
minMmap=min(MMAP($\beta$)) for all $\beta$'s in a reconstruction view range
Based upon the maxMmap value and the minMmap value, MMAP values are normalized and plotted as illustrated in FIG. 4B. The normalized MMAP values range between 0 and 1.0. One example of the vMMAP weighting function, $u_{vMMAP}(\beta)$ is defined in Equation (7B):

$$u_{vMMAP}(\beta) = p\left(\frac{maxMmap - vMMAP(\beta)}{maxMmap - minMmap}\right) \quad (7B)$$

where p( ) is generally a function that satisfies the following conditions: p(0)=0, p(1)=1, and p(x) also monotonically increases from 0 to 1 as the variable x increases. Some examples of the function p( ) include a linear equation p(x)=x, a polynomial equation such as p(x)=3x²-2x³ and a trigonometric equation such as $$p(x) = \frac{1}{2}(1 - \cos(\pi x)) \text{ or } p(x) = \sin^2\left(\frac{\pi x}{2}\right).$$

In summary, as shown in FIGS. 4A and 4B, the more weight value is assigned to a view that has a less amount of motion while the less weight value is assigned to a view that has a more amount of motion. By the same token, the highest weight value 1 in FIG. 4B is assigned to a view that has the least amount of motion as indicated by min Mmap in FIG. 4A while the lowest weight value 0 in FIG. 4B is assigned to a view that has the most amount of motion as indicated by max Mmap in FIG. 4A.

Finally, the processing unit or step performs tasks of weighting projection data acquired during circular trajectory of a cone beam source according to the above determined normalized vMMAP weight value. That is, each of the projection data pd ($\beta$, $\gamma$, v) is weighted by the normalized vMMAP weight value $w_{vMMAP}(\beta,\gamma)$, which has been determined for a corresponding view $\beta$ and a corresponding fan angle $\gamma$. The above determined weight value in effect selects the most valid views of all complementary views.

Although the above embodiment is described with respect to cardiac motion, the same concept is applicable to lung motion. Since lung data is generally collected at a faster rate than cardiac data, redundant data may not be sufficiently available for gated reconstruction or may be available for a very limited gated reconstruction. Furthermore, unlike ECG for cardiac data, no outside motion information is available for reconstruction.

In a third embodiment, the processing unit or step performs tasks of weighting projection data that has been acquired during a circular trajectory of a cone beam source according to a motion map. The third embodiment includes both 2D and 3D cases. In general, after acquiring the projection data using a cone beam along a circular trajectory, the processing unit or step ultimately determines a normalized weighting value according to a ray-based motion map (rMMAP) weighting function. The ray-based motion map (rMMAP) weighting function is utilized in cases where redundant data without outside motion information such as ECG may not be sufficiently available for gated reconstruction or may be available only for a very limited gated reconstruction.

The rMMAP weighting $w_{rMMAP}(\beta,\gamma)$ is function of view angle $\beta$ and fan angle $\gamma$ and is normalized as defined below in Equation (8).

$$w_{rMMAP}(\beta, \gamma) = \frac{u_{rMMAP}(\beta, \gamma)}{\sum_{n=-N_{PI}}^{N_{PI}} u_{rMMAP}(\beta_n^C, \gamma_n^C)} \quad (8)$$

In general, the normalized rMMAP weighting function $w_{rMMAP}(\beta,\gamma)$ is determined by normalizing rMMAP weighting function, $u_{rMMAP}(\beta,\gamma)$ over a summation of $u_{rMMAP}(\beta_n^C, \gamma_n^C)$ from $n=-N_{PI}$ to $n=N_{PI}$ for complementary view angles ($\beta_n^C, \gamma_n^C$). The value of $n=N_{PI}$ is determined to be as large as necessary to take into account all available cardiac data. One exemplary definition of the complementary view angles ($\beta_n^C$) is defined by Equation (4). One exemplary definition of the complementary view angles ($\gamma_n^C$) is defined by Equation (9).

$$\gamma_n^C(\gamma) = \begin{cases} -\gamma, & n \text{ odd} \\ \gamma, & n \text{ even} \end{cases} \quad (9)$$

The normalized rMMAP weighting function $w_{rMMAP}(\beta,\gamma)$ determines a weight value ranging from 0 to 1 with respect to a particular view angle $\beta$ and a particular fan $\gamma$.

Figure 6:
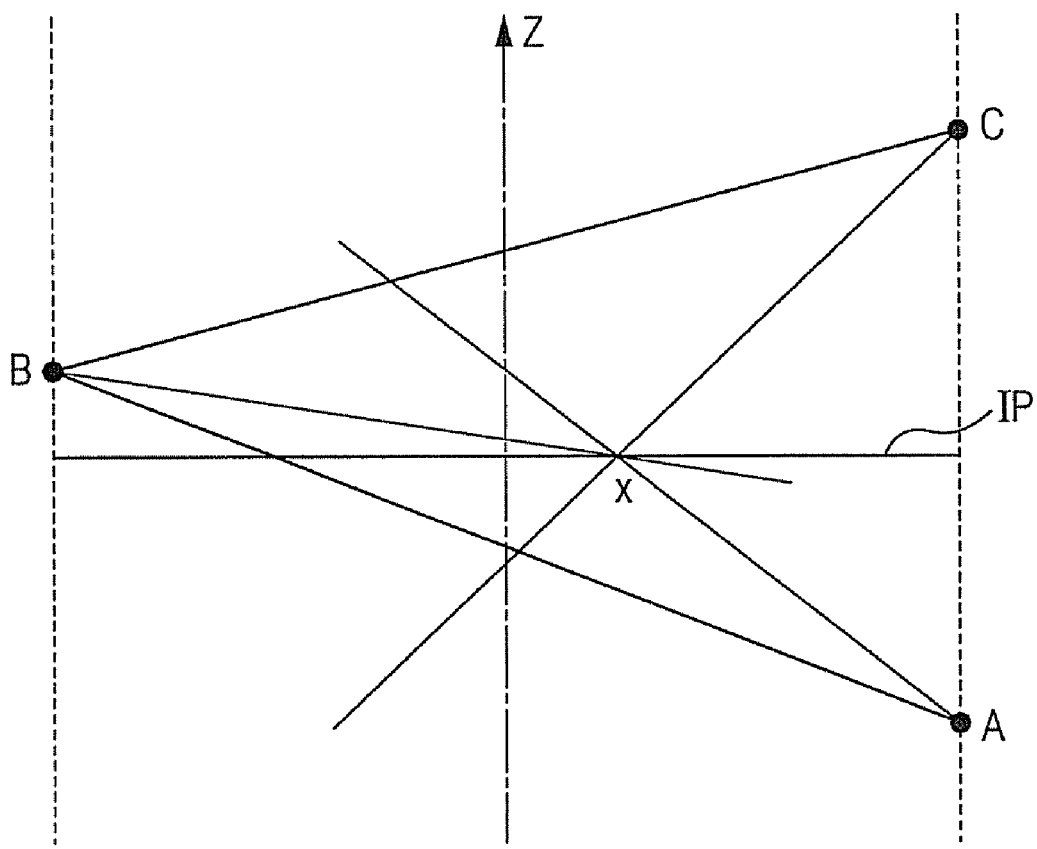
FIG. 6 is a diagram illustrating views and an image plane for a ray-based motion map.

In one example, the ray-based motion map rMMAP weighting function $u_{rMMAP}(\beta,\gamma)$ is ultimately evaluated based upon the following ray-based motion maps. Referring to FIG. 6, a diagram illustrates a vertical plane where three source positions or views A, B and C exist. Ray BC corresponds to PI-boundary, and ray CB is exactly complementary to the ray BC. By the same token, ray BA corresponds to PI-boundary, and ray AB is exactly complementary to the ray BA. In addition, the diagram also shows ray Bx, which is emitted from the source B and passes through a pixel x on an image plane IP. Rays Ax and Cx are the complementary rays of the ray Bx. For the purpose of the current invention, motion on the rays AB and BC is respectively estimated based upon the in Equations (10A) and (10B).

$$m(AB) = f(|g(BA) - g(AB)|) \quad (10A)$$

$$m(BC) = f(|g(CB) - g(BC)|) \quad (10B)$$

where $g(.)$ is measured raw data such as projection data while $f(.)$ is a predetermined function such that $f(0)=1$ and $f(t) \to 0$ as $t$ increases. For example, $f(.)$ is defined as:

$$f(t) = \exp\left(-\frac{t^2}{\delta^2}\right)$$

In order to assign a weight value, at each view or source position A, B and C according to the above estimated ray-based motion, the ray-based motion map rMMAP weighting function $u_{rMMAP}(\beta,\gamma)$ is evaluated based upon the following assumptions and rule. It is assumed that the quietest phase is always near the center of the view range. In other words, it is assumed that the quietest phase is near the image plane IP. This assumption is necessary for reconstruction. Thus, one exemplary evaluation or assignment rule is that a view closest to the image plane IP is always assigned a motion weight value of 1. In this example as illustrated in FIG. 6, the motion weight value of 1 is assigned to the view or source position B since the view B is the closest to the image plane IP and near the center of the view range.

By using the simplified notation, the ray-based motion map rMMAP weighting function $u_{rMMAP}(\beta,\gamma)$ is expressed as follows at each of the views A, B and C: $u_{rMMAP}(A) = u_{rMMAP}(\beta_A,\gamma_A)$, $u_{rMMAP}(B) = u_{rMMAP}(\beta_B,\gamma_B)$, $u_{rMMAP}(C) = u_{rMMAP}(\beta_C,\gamma_C)$. Based upon the above described assumption and the rule, the ray-based motion map weight values are determined as follows by Equations 11A, 11B and 11C using the example as illustrated in FIG. 6:

$$u_{rMMAP}(B) = 1 \quad (11A)$$

$$u_{rMMAP}(A) = m(AB) \quad (11B)$$

$$u_{rMMAP}(C) = m(BC) \quad (11C)$$

In confirming the weight values, a sum of the weight values should be one for the rays passing through a particular pixel on the image plane IP. In the example as illustrated in FIG. 6, a sum of the weight values should be one for the rays Ax, Bx and Cx passing through the pixel x on the image plane IP.

In summary, the more weight value is assigned to a ray that has a less amount of motion while the less weight value is assigned to a ray that has a more amount of motion. By the same token, the highest weight value 1 is assigned to a ray that has the least amount of motion while the lowest weight value 0 is assigned to a ray that has the most amount of motion.

Finally, the processing unit or step performs tasks of weighting projection data acquired during circular trajectory of a cone beam source according to the above determined normalized rMMAP weight value. That is, each of the projection data pd ($\beta$, $\gamma$, v) is weighted by the normalized rMMAP weight value $w_{rMMAP}(\beta,\gamma)$, which has been determined for a corresponding view $\beta$ and a corresponding fan angle $\gamma$. The above determined weight value in effect selects the most valid views of all complementary views.

Although the above embodiment is described with respect to cardiac motion, the same concept is applicable to lung motion. Since lung data is generally collected at a faster rate than cardiac data, redundant data may not be sufficiently available for gated reconstruction or may be available for a very limited gated reconstruction. Furthermore, unlike ECG for cardiac data, no outside motion information is available for reconstruction.

In addition to the above described motion weighting, each of the first, second and third embodiments additionally weight the projection data based upon a fan angle of the cone beam according to the current invention. The additional weighting may be either simultaneous or sequential in these embodiments with respect to the above described motion weighting.

In addition to the above described motion weighting, each of the first, second and third embodiments additionally weight the projection data based upon a fan angle of the cone beam according to the current invention. The additional fan beam weighting $w_{FB}(\beta,\gamma)$ is also function of view angle $\beta$ and fan angle $\gamma$ and is normalized as defined below in Equation (12).

$$w_{FB}(\beta, \gamma) = \frac{u_{FB}(\beta)}{\sum_{n=-N_{PI}}^{N_{PI}} u_{FB}(\beta_n^C, \gamma_n^C)} \quad (12)$$

In general, the normalized FB weighting function $w_{FB}(\beta,\gamma)$ is determined by normalizing FB weighting function, $u_{FB}(\beta)$ over a summation of $u_{FB}(\beta_n^C,\gamma_n^C)$ from $n=-N_{PI}$ to $n=N_{PI}$ for complementary view angles $(\beta_n^C,\gamma_n^C)$. One exemplary definition of the complementary view angles $(\beta_n^C)$ is defined by Equation (4). One exemplary definition of the complementary view angles $(\gamma_n^C)$ is defined by Equation (9). The value of $n=N_{PI}$ is determined to be as large as necessary to take into account all available cardiac data. The normalized FB weighting function $w_{FB}(\beta,\gamma)$ determines a weight value ranging from 0 to 1 with respect to a particular view angle $\beta$ and a particular fan $\gamma$.

Figure 8A:
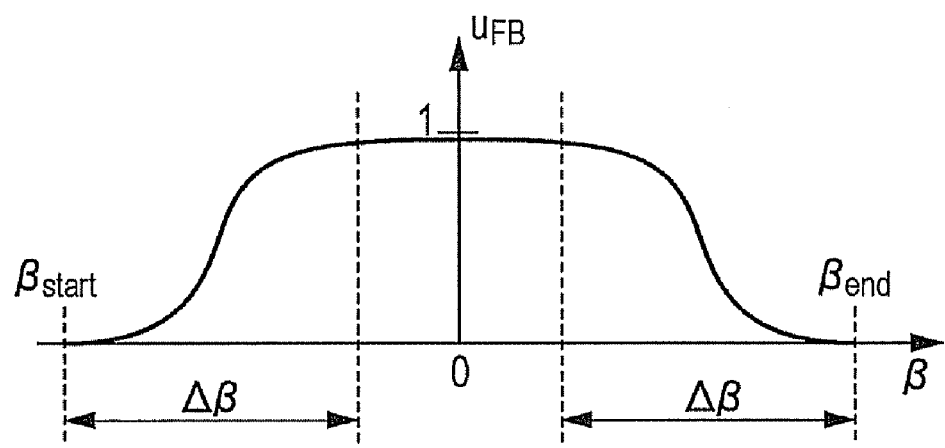
FIG. 8A is an example of a fan beam weighting function.

In one example, the FB fan beam weighting function, $u_{FB}(\beta)$ is ultimately evaluated based upon the following exemplary Equation (13). As illustrated in FIG. 8A, an example of the FB fan beam weighting function, $u_{FB}(\beta)$ determines a weight value between 0 and 1 for each view.

$$u_{FB}(\beta) = \begin{cases} 0, & \beta < \beta_{start} \\ p\left(\dfrac{\beta - \beta_{start}}{\Delta\beta}\right), & \beta_{start} \leq \beta < \beta_{start} + \Delta\beta \\ 1, & \beta_{start} + \Delta\beta \leq \beta \leq \beta_{end} - \Delta\beta \\ p\left(\dfrac{\beta_{end} - \beta}{\Delta\beta}\right), & \beta_{end} - \Delta\beta < \beta \leq \beta_{end} \\ 0, & \beta > \beta_{end} \end{cases} \quad (13)$$

where $\Delta\beta$ is a predetermined smoothing interval in terms of a fixed number of views, a fixed angular range such as 10°, or a percentage of the angular reconstruction range such as ($\beta_{end}$−$\beta_{start}$). $\beta_{start}$ and $\beta_{end}$ together determine the image reconstruction view range. In certain embodiments, the smoothing interval is optionally as small as 0% or as large as 50%. In addition, the function p( ) is optionally defined in various ways. For example, the function p( ) is one of the following equations:

Linear: $p(x) = x$.

Polynomial: $p(x) = 3x^2 - 2x^3$.

Trigonometric: $p(x) = \dfrac{1}{2}(1 - \cos(\pi x))$ or $p(x) = \sin^2\left(\dfrac{\pi x}{2}\right)$ In general, the function p(t) is any function that satisfies: p(0)=0, p(1)=1, and p p(t) monotonically increases as t increases from 0 to 1.

In the first embodiment, the processing unit or step performs tasks of additionally weighting the projection data that has been acquired during a circular trajectory of a cone beam source according to the cardiac phase. As described above, the processing unit or step ultimately determines a weighting value according the fan beam weighting FB in addition to the electrocardiogram gated reconstruction (EGR) weighting function.

For use in the first embodiment, the FB+EGR weighting function $w_{FB+EGR}(\beta,\gamma)$ is function of view angle $\beta$ and fan angle $\gamma$ and is normalized as defined below in Equation (14).

$$w_{FB+EGR}(\beta, \gamma) = \dfrac{u_{FB}(\beta)u_{EGR}(\varphi(\beta))}{\sum_{n=-N_{PI}}^{N_{PI}} u_{FB}(\beta_n^C, \gamma_n^C) u_{EGR}(\varphi(\beta_n^C))} \quad (14)$$

In general, the normalized FB+EGR weighting function $w_{FB+EGR}(\beta,\gamma)$ is determined by normalizing FB function $u_{FB}(\beta)$ and EGR weighting function, $u_{EGR}(\phi(\beta))$ over a summation of $u_{FB}(\beta_n^C,\gamma_n^C)$ and $u_{EGR}(\phi(\beta_n^C))$ from n=−$N_{PI}$ to n=$N_{PI}$ for complementary view angles ($\beta_n^C$). One exemplary definition of the complementary view angles ($\beta_n^C$) is defined by Equation (4). One exemplary definition of the complementary view angles ($\gamma_n^C$) is defined by Equation (9). The value of n=$N_{PI}$ is determined to be as large as necessary to take into account all available cardiac data. The normalized EGR weighting function $w_{FB+EGR}(\beta,\gamma)$ determines a weighting value ranging from 0 to 1 with respect to a particular view angle $\beta$ and a particular fan angle $\gamma$.

In the second embodiment, the processing unit or step performs tasks of additionally weighting the projection data that has been acquired during a circular trajectory of a cone beam source according to the cardiac phase. As described above, the processing unit or step ultimately determines a weighting value according the fan beam weighting FB in addition to the view-based motion map (vMMAP) weighting function.

For use in the second embodiment, the FB+vMMAP weighting function is normalized and designated by $w_{FB+vMMAP}(\beta,\gamma)$ as defined below in Equation (15).

$$w_{FB+vMMAP}(\beta, \gamma) = \dfrac{u_{FB}(\beta)u_{vMMAP}(\beta)}{\sum_{n=-N_{PI}}^{N_{PI}} u_{FB}(\beta_n^C, \gamma_n^C) u_{vMMAP}(\beta_n^C)} \quad (15)$$

In general, the normalized FB+vMMAP weighting function $w_{FB+vMMAP}(\beta,\gamma)$ is determined by normalizing FB function $u_{FB}(\beta)$ and view-based motion map vMMAP weighting function, $u_{vMMAP}(\beta)$ over a summation of $u_{FB}(\beta_n^C,\gamma_n^C)$ and $u_{vMMAP}(\beta_n^C)$ from n=−$N_{PI}$ to n=$N_{PI}$ for complementary view angles ($\beta_n^C$). One exemplary definition of the complementary view angles ($\beta_n^C$) is defined by Equation (4). One exemplary definition of the complementary view angles ($\gamma_n^C$) is defined by Equation (9). The value of n=$N_{PI}$ is determined to be as large as necessary to take into account all available cardiac data. The normalized FB+vMMAP weighting function $w_{FB+vMMAP}(\beta,\gamma)$ determines a weighting value ranging from 0 to 1 with respect to a particular view angle $\beta$ and a particular fan angle $\gamma$.

Figure 5A:
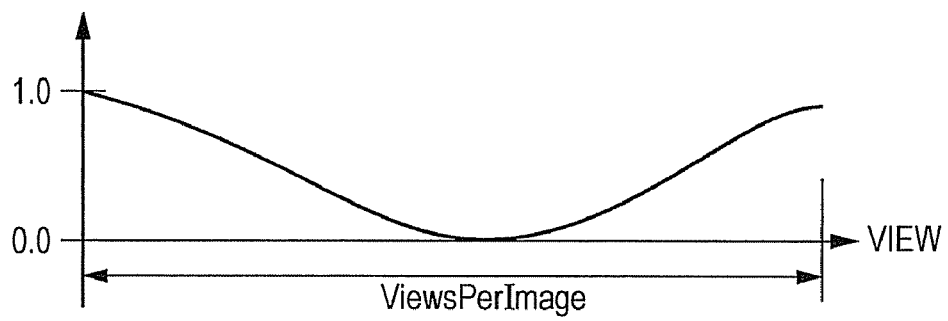
FIG. 5A is a graph illustrating the normalized motion map of FIG. 4B.
Figure 5B:
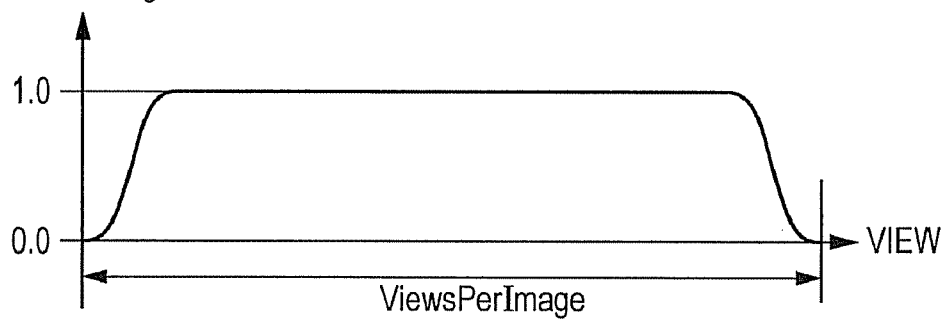
FIG. 5B is a graph illustrating an additional fan beam weighting within the viewsPerImage range.
Figure 5C:
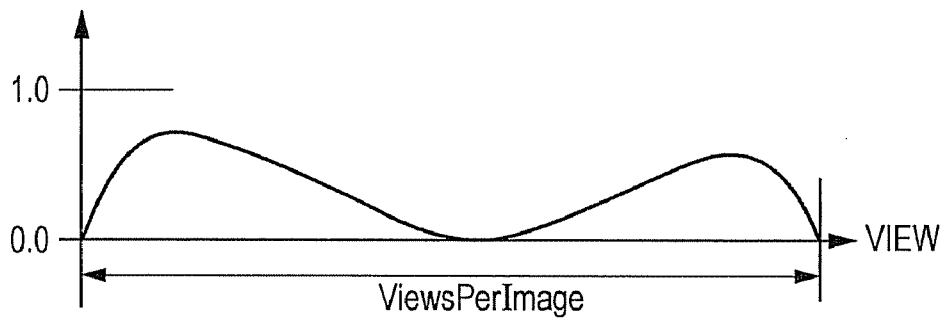
FIG. 5C is a graph illustrating the combined normalized and fan beam weighting.

Now referring to FIGS. 5A, 5B and 5C, the graphs illustrate a process of further weighting the normalized projection data. The graph in FIG. 5A illustrates a normalized motion map of FIG. 4B. The max motion map (maxMmap) value and the minimal motion map (minMmap) value are normalized so that their values are respectively 0 and 1. The graph in FIG. 5B illustrates the additional fan beam weighting $w_{FB}(\beta,\gamma)$ function as defined above in Equation (12) within the viewsPerImage range. Towards the ends of the viewsPerImage range, the fan beam weighting $w_{FB}(\beta,\gamma)$ function approaches a minimal value of zero. The graph in FIG. 5C illustrates the combined normalized FB+vMMAP weighting function $w_{FB+vMMAP}(\beta,\gamma)$ as defined below in Equation (15) within the viewsPerImage range.

In the third embodiment, the processing unit or step performs tasks of additionally weighting the projection data that has been acquired during a circular trajectory of a cone beam source according to the cardiac phase. As described above, the processing unit or step ultimately determines a weighting value according the fan beam weighting FB in addition to the ray-based motion map (rMMAP) weighting function.

For use in the third embodiment, the FB+rMMAP weighting function is normalized and designated by $w_{FB+rMMAP}(\beta,\gamma)$ as defined below in Equation (16).

$$w_{FB+rMMAP}(\beta, \gamma) = \dfrac{u_{FB}(\beta)u_{rMMAP}(\beta, \gamma)}{\sum_{n=-N_{PI}}^{N_{PI}} u_{FB}(\beta_n^C, \gamma_n^C) u_{rMMAP}(\beta_n^C, \gamma_n^C)} \quad (16)$$

In general, the normalized FB+rMMAP weighting function $w_{FB+rMMAP}(\beta,\gamma)$ is determined by normalizing FB function $u_{FB}(\beta)$ and ray-based motion map rMMAP weighting function, $u_{rMMAP}(\beta,\gamma)$ over a summation of $u_{FB}(\beta_n^C,\gamma_n^C)$ and $u_{rMMAP}(\beta_n^C,\gamma_n^C)$ from n=−$N_{PI}$ to n=$N_{PI}$ for complementary view and fan angles ($\beta_n^C,\gamma_n^C$). One exemplary definition of the complementary view angles ($\beta_n^C$) is defined by Equation (4). One exemplary definition of the complementary fan angles ($\gamma_n^C$) is defined by Equation (9). The value of n=$N_{PI}$ is determined to be as large as necessary to take into account all available cardiac data. The normalized FB+rMMAP weighting function $w_{FB+rMMAP}(\gamma,\gamma)$ determines a weighting value ranging from 0 to 1 with respect to a particular view angle $\beta$ and a particular fan angle $\gamma$.

The above described combinations of the weighting functions is merely exemplary, and other embodiments of the current invention optionally weight the projection data based upon combinations other than the above described weighting functions. One such example is FB+vMMAP+EGR weighting function and includes a combination of the fan angle FB function $u_{FB}(\beta,v)$, view-based motion map vMMAP weighting function $u_{vMMAP}(\beta)$ and electrocardiogram gated reconstruction EGR weighting function $u_{EGR}(\phi(\beta))$. In this example, the combined weighting function is based upon two motion indexes such as view-based motion map and electrocardiogram gated reconstruction and a fan beam index.

The FB+vMMAP+EGR weighting function is normalized and designated by $w_{FB+vMMAP+EGR}(\beta,\gamma)$ as defined below in Equation (17).

$$w_{FB+vMMAP+EGR}(\beta, \gamma) = \frac{u_{FB}(\beta)u_{vMMAP}(\beta)u_{EGR}(\varphi(\beta))}{\sum_{n=-N_{PI}}^{N_{PI}} u_{FB}(\beta_n^C, \gamma_n^C)u_{vMMAP}(\beta_n^C)u_{EGR}(\varphi(\beta_n^C))} \quad (17)$$

In general, the normalized FB+vMMAP+EGR weighting function $w_{FB+vMMAP+EGR}(\beta,\gamma)$ is determined by normalizing FB function $u_{FB}(\beta,v)$, view-based motion map vMMAP weighting function $u_{vMMAP}(\beta)$ and EGR weighting function $u_{EGR}(\phi(\beta))$ over a summation of $u_{FB}(\beta_n^C,\gamma_n^C)$, $u_{vMMAP}(\beta_n^C)$ and $u_{EGR}(\phi(\beta_n^C))$ from $n=-N_{PI}$ to $n=N_{PI}$ for complementary view angles $(\beta_n^C)$. One exemplary definition of the complementary view angles $(\beta_n^C)$ is defined by Equation (4). One exemplary definition of the complementary view angles $(\gamma_n^C)$ is defined by Equation (9). The value of $n=N_{PI}$ is determined to be as large as necessary to take into account all available cardiac data. The normalized FB+vMMAP+EGR weighting function $w_{FB+vMMAP+EGR}(\beta,\gamma)$ determines a weighting value ranging from 0 to 1 with respect to a particular view angle $\beta$ and a particular fan angle $\gamma$.

In another example, a FB+rMMAP+EGR weighting function includes a combination of the fan beam FB function $u_{FB}(\beta,v)$, ray-based motion map rMMAP weighting function $u_{rMMAP}(\beta,\gamma)$ and electrocardiogram gated reconstruction EGR weighting function $u_{EGR}(\phi(\beta))$. In this example, the combined weighting function is based upon two motion indexes such as rau-based motion map and electrocardiogram gated reconstruction and a fan beam index.

The FB+rMMAP+EGR weighting function is normalized and designated by $w_{FB+rMMAP+EGR}(\beta,\gamma)$ as defined below in Equation (18).

$$w_{FB+rMMAP+EGR}(\beta, \gamma) = \frac{u_{FB}(\beta)u_{rMMAP}(\beta, \gamma)u_{EGR}(\varphi(\beta))}{\sum_{n=-N_{PI}}^{N_{PI}} u_{FB}(\beta_n^C, \gamma_n^C)u_{rMMAP}(\beta_n^C, \gamma_n^C)u_{EGR}(\varphi(\beta_n^C))} \quad (18)$$

In general, the normalized FB+rMMAP+EGR weighting function $w_{FB+rMMAP+EGR}(\beta,\gamma)$ is determined by normalizing FB function $u_{FB}(\beta,v)$, ray-based motion map rMMAP weighting function $u_{rMMAP}(\beta,\gamma)$ and EGR weighting function $u_{EGR}(\phi(\beta))$ over a summation of $u_{FB}(\beta_n^C,\gamma_n^C)$, $u_{rMMAP}(\beta_n^C, \gamma_n^C)$ and $u_{EGR}(\phi(\beta_n^C))$ from $n=-N_{PI}$ to $n=N_{PI}$ for complementary view and fan angles $(\beta_n^C,\gamma_n^C)$. One exemplary definition of the complementary view angles $(\beta_n^C)$ is defined by Equation (4). One exemplary definition of the complementary view angles $(\gamma_n^C)$ is defined by Equation (9). The value of $n=N_{PI}$ is determined to be as large as necessary to take into account all available cardiac data. The normalized FB+rMMAP+EGR weighting function $w_{FB+rMMAP+EGR}(\beta,\gamma)$ determines a weighting value ranging from 0 to 1 with respect to a particular view angle $\beta$ and a particular fan angle $\gamma$.

In the second group of embodiments, projection data is weighted based upon a combination of at least a single motion index and cone beam characteristics, and the projection data is acquired using a cone beam source in a helical path. The second group of embodiments also weights projection data based upon a combination of multiple motion indexes and cone beam characteristics, and the projection data is acquired using a cone beam source in a helical path. The cone beam characteristics used in the second group of embodiments include weighting based upon a combination of a fan angle and a cone angle.

Figure 7:
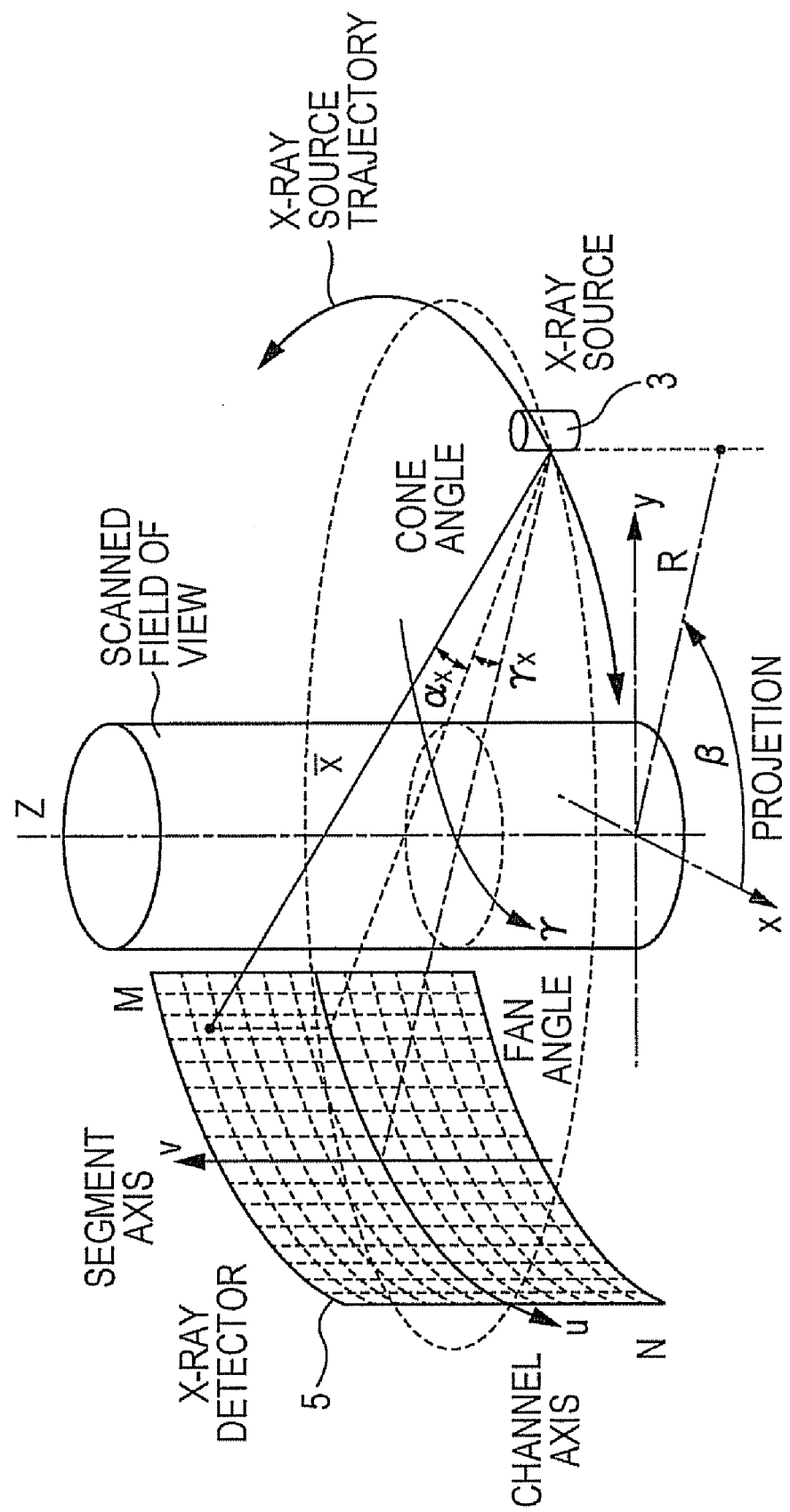
FIG. 7 is a diagram illustrating the system geometry for a cone-beam system for helical data acquisition according to the invention.

Now referring to FIG. 7, a diagram illustrates the system geometry for a cone-beam system for and a method of helical data acquisition according to the invention. In general, X-rays are emitted from the X-ray source 3 at a plurality of projection angles around the object to collect at least minimally required tomographic data. At each of a projection angle $\beta$ with respect to the x axis, x-rays are emitted with a cone angle $\alpha$ and a fan angle $\gamma$ and pass through an object with a scanned field of view. The source 3 and the two-dimensional detector 5 are diametrically positioned across the rotating axis. As the source 3 travels over a predetermined helical path, the two-dimensional detector 5 detects the x-rays. The predetermined helical trajectory of the source 3 with a helical pitch H is defined by $\lambda(\beta)=(R\cos(\beta-\beta_0), R\sin(\beta-\beta_0), (\beta-\beta_0)H/2\pi)$, where R is the radius of the source trajectory while $\beta_0$ is an initial projection angle.

Still referring to FIG. 7, using the cone beam, each ray is uniquely defined by $(\beta, \gamma, v)$, where $\beta$ is the projection or view angle, $\gamma$ is the fan angle and v is the detector coordinate parallel to the axis of rotation. That is, $v=R\tan\alpha$, where $\alpha$ is the cone angle. It is assumed that a cylindrical detector as defined by $(\gamma, v)$ is focused on the source $\lambda(\beta)$ at distance R. The two-dimensional detector 5 is described to have a detector element k from k=1 to N·M, where N is the number of detector rows while M is the number of elements per detector row.

For each data sample (view, ch, seg) and the corresponding ray $(\beta, \gamma, v)$, the cone beam weight is determined in the following manner. In a first step, cone beam complementary rays $(\beta_n^C,\gamma_n^C,v_n^C)$ are determined such that they intersect the reconstruction image plane at the same point as the direct rays $(\beta, \gamma, v)$. When the summation index n=0, complementary rays $(\beta_n^C,\gamma_n^C,v_n^C)$ correspond to the direct rays $(\beta, \gamma, v)$. That is, $\beta_0=\beta$, $\gamma_0=\gamma$, $v_0=v$, $\Delta z_0=\beta_S-\beta$. The complementary ray coordinates are defined as follows by Equations (19A), (19B) and (19C).

$$\beta_n^C(\beta, \gamma) = \begin{cases} \beta + 2\gamma + n\pi, & n \text{ odd} \\ \beta + 2n\pi, & n \text{ even} \end{cases} \quad (19A)$$

$$v_n^C(\beta, \gamma, v) = \begin{cases} \Delta z_n R/L^C, & n \text{ odd} \\ \Delta z_n R/L, & n \text{ even} \end{cases} \quad (19B)$$

$$\gamma_n^C(\gamma) = \begin{cases} -\gamma, & n \text{ odd} \\ \gamma, & n \text{ even} \end{cases} \quad (19C)$$

where $\Delta z_n = \Delta \beta_n H/2\pi$, $\Delta \beta_n = \beta_S - \beta_n$, $\beta_S$ is the view angle corresponding to the image slice position, $L = \Delta z_0 R/v$ and $L^c = 2R\cos\gamma - L$. The image plane is given by $z = z_S$, and $\beta_S = \beta_0 + 2\pi z_S/H$.

In a second step of determining the cone beam weight value, the projection data $g(\beta, \gamma, v)$ is weighted depending on the ray position and normalize by the weighted contributions of all complementary rays. Thus, the normalized cone beam weighting CBW function $w_{CBW}(\beta, \gamma, v)$ is defined by Equation (20):

$$w_{CBW}(\beta, \gamma, v) = \frac{u_{CBW}(\beta, v)}{\sum_{n=-N_{PI}}^{N_{PI}} u_{CBW}(\beta_n^C, \gamma_n^C, v_n^C)} \quad (20)$$

In general, the normalized cone beam CBW weighting function $w_{CBW}(\beta, \gamma, v)$ is determined by normalizing cone beam CB function $u_{CBW}(\beta, v)$ over a summation of $u_{CBW}(\beta_n^C, \gamma_n^C, v_n^C)$ from $n = -N_{PI}$ to $n = N_{PI}$ for complementary view angles, complementary fan angles and complementary detector coordinates $w_{CBW}(\beta, \gamma, v)$. One exemplary definition of the complementary view angles $(\beta_n^C)$ is defined by Equation (4) or (19A). One exemplary definition of the complementary detector coordinates $(v_n^C)$ is defined by the following Equation (19B). One exemplary definition of the complementary fan angle $(\gamma_n^C)$ is defined by the following Equation (9) or (19C). The value $N_{PI}$ is the number of helical turns (half-rotations) used for image reconstruction. The value of $n = N_{PI}$ is determined to be as large as necessary to take into account all available cardiac data. The normalized CBW weighting function $w_{CBW}(\beta, \gamma, v)$ determines a weighting value ranging from 0 to 1 with respect to a particular view angle $\beta$, a particular fan angle $\gamma$ and a particular vertical coordinate $v$.

In further detail, the cone beam weighting CBW function is a product of the two weighting functions as defined in Equation (21) as follows:

$$u_{CBW}(\beta, v) = u_{FB}(\beta, \gamma) u_{CB}(v) \quad (21)$$

Figure 8B:
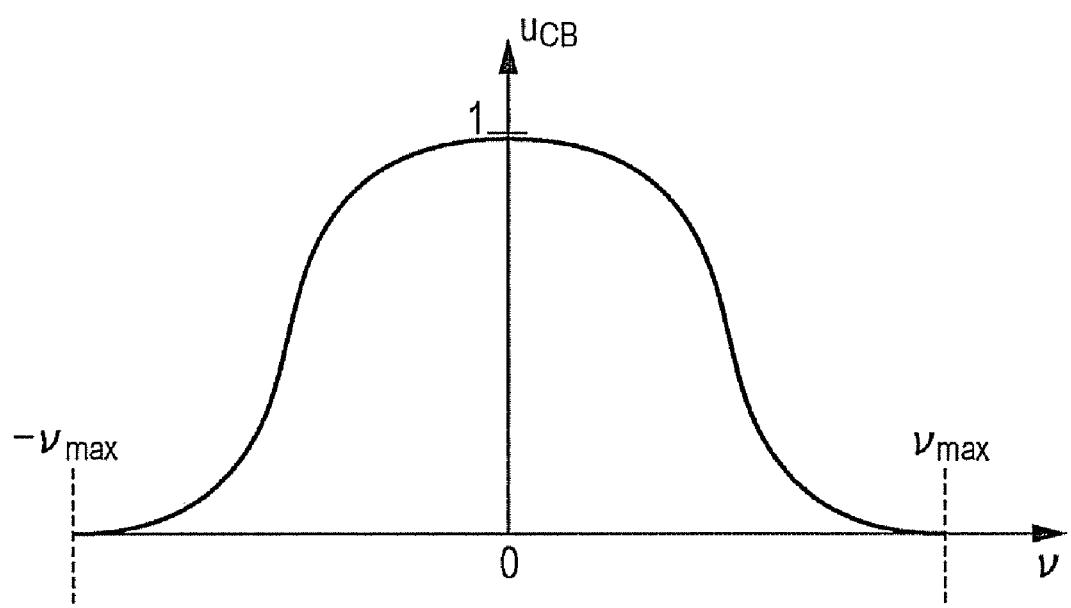
FIG. 8B is an example of a cone beam weighting function.

The fan beam FB weighting function $u_{FB}(\beta, \gamma)$ and the cone beam CB weighting function $u_{CB}(v, \gamma)$ are called auxiliary weighting functions. Examples of fan beam FB weighting function $u_{FB}(\beta, \gamma)$ and the cone beam CB weighting function $u_{CB}(v)$ are respectively illustrated in FIGS. 8A and 8B.

As already described above, the fan beam FB weighting function $u_{FB}(\beta, \gamma)$ is implemented in various ways. One example of the fan beam FB weighting function $u_{FB}(\beta, \gamma)$ has been already given in Equation (13).

By the same token, the cone beam CB weighting function $u_{CB}(v, \gamma)$ is also implemented in various ways. One example of the cone beam CB weighting function $u_{CB}(v)$ is given in Equation (22) below.

$$u_{CB}(v) = \begin{cases} 0, & v \leq -W \\ p\left(\frac{W+v}{\Delta v}\right), & -W < v < -W + \Delta v \\ 1, & -W + \Delta v \leq v \leq W - \Delta v \\ p\left(\frac{W-v}{\Delta v}\right), & W - \Delta v < v < W \\ 0, & v \geq W \end{cases} \quad (22)$$

where $\Delta v$ is a predetermined smoothing interval in terms of a fixed length such as 3.2 mm or 3.2 segments, or a percentage of the detector height 2 W. In certain embodiments, the smoothing interval is optionally as small as 0% or as large as 50%. In addition, the function $p(\ )$ is optionally defined in various ways. For example, the function $p(\ )$ is one of the following equations:

Linear: $p(x) = x$.

Polynomial: $p(x) = 3x^2 - 2x^3$.

Trigonometric: $p(x) = \frac{1}{2}(1 - \cos(\pi x))$ or $p(x) = \sin^2\left(\frac{\pi x}{2}\right)$ In general, the function $p(t)$ is any function that satisfies: $p(0) = 0$, $p(1) = 1$, and $p$ $p(t)$ monotonically increases as $t$ increases from 0 to 1.

Figure 9:
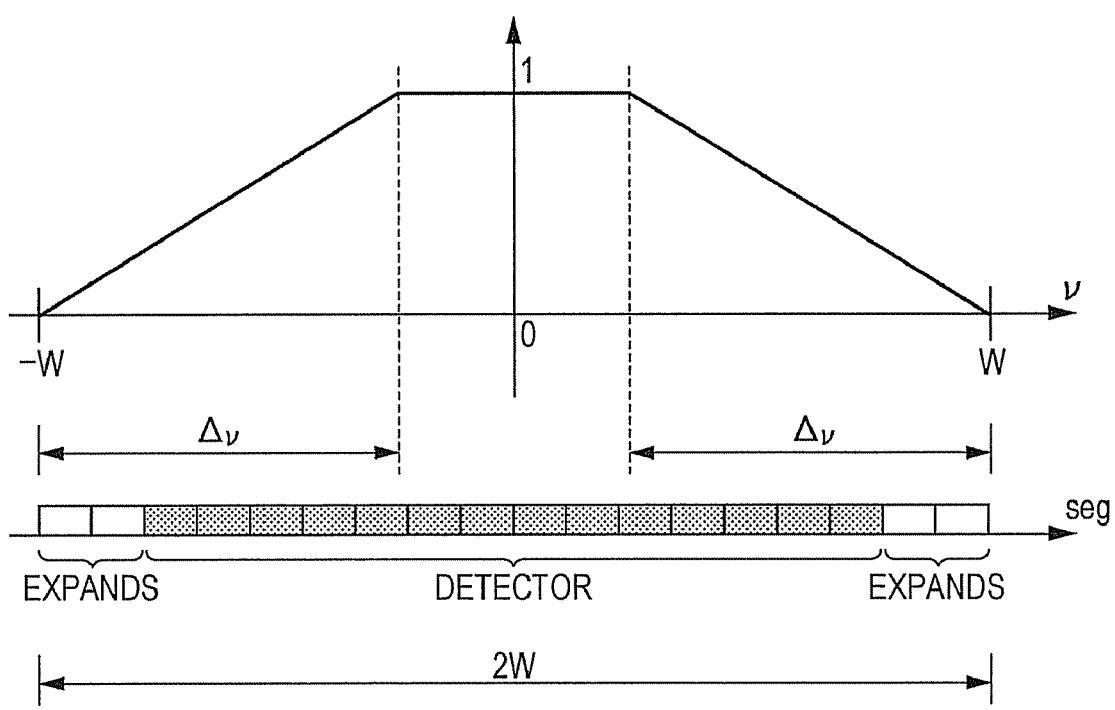
FIG. 9 is a diagram illustrating detector coordinates with respect to a predetermined smoothing interval.

Now referring to FIG. 9, a row of the detector elements is illustrated with respect to a predetermined smoothing interval. The detector is expanded to the detector height 2 W from its original size that is less than the height 2 W as indicated by the portions that are marked as "expands." With the expanded height 2 W, a smoothing interval $\Delta v$ is also expanded so that the smoothing function now has a larger or smoother rate of change within the expanded height 2 W.

In the fourth embodiment, the processing unit or step performs tasks of additionally weighting the projection data that has been acquired during a helical trajectory of a cone beam source according to the cardiac phase. Although patches for electrocardiogram-gated reconstruction (EGR) are selected without regard to the cone angle in certain embodiments, a cone beam weighting (CBW) technique is optionally extended to include EGR and cardiac motion information in other embodiments. As described above, the processing unit or step ultimately determines a weighting value according the normalized cone beam weighting CBW in addition to the normalized electrocardiogram gated reconstruction (EGR) weighting function.

For use in the fourth embodiment, the CBW+EGR weighting function $w_{CBW+EGR}(\beta, \gamma, v)$ is function of view angle $\beta$, fan angle $\gamma$ and vertical coordinate of the detector $v$ and is normalized as defined below in Equation (23).

$$w_{CBW+EGR}(\beta, \gamma, v) = \frac{u_{CBW}(\beta, v) u_{EGR}(\varphi(\beta))}{\sum_{n=-N_{PI}}^{N_{PI}} u_{CBW}(\beta_n^C, \gamma_n^C, v_n^C) u_{EGR}(\varphi(\beta_n^C))} \quad (23)$$

In general, the normalized CBW+EGR weighting function $w_{CBW+EGR}(\beta, \gamma, v)$ is determined by normalizing CBW function $u_{CBW}(\beta, v)$ and EGR weighting function, $u_{EGR}(\phi(\beta))$ over a summation of $u_{CBW}(\beta_n^C, \gamma_n^C, v_n^C)$ and $u_{EGR}(\phi(\beta_n^C))$ from $n = -N_{PI}$ to $n = N_{PI}$ for complementary parameters $(\beta_n^C, \gamma_n^C, v_n^C)$.

For the definitions of the above functions, previously provided equations are referenced. For example, the normalized cone beam weighting CBW function $w_{CBW}(\beta,\gamma,v)$ is defined by Equation (20). The normalized electrocardiogram gated reconstruction EGR weighting function $w_{EGR}(\beta,\gamma)$ is defined in Equation (3). One exemplary definition of the complementary view angles $(\beta_n^C)$ is defined by Equation (4) or (19A). One exemplary definition of the complementary detector coordinates $(v_n^C)$ is defined by the following Equation (19B). One exemplary definition of the complementary fan angle $(\gamma_n^C)$ is defined by the following Equation (9) or (19C). The value of $n=N_{PI}$ is determined to be as large as necessary to take into account all available cardiac data. The normalized CBW+EGR weighting function $w_{CBW+EGR}(\beta,\gamma,v)$ determines a weighting value ranging from 0 to 1 with respect to a particular view angle $\beta$, a particular fan angle $\gamma$ and a particular vertical coordinate v.

In the fifth embodiment, the processing unit or step performs tasks of additionally weighting the projection data that has been acquired during a helical trajectory of a cone beam source according to a view-based motion map vMMAP. A cone beam weighting (CBW) technique is optionally extended to include vMMAP. As described above, the processing unit or step ultimately determines a weighting value according the normalized cone beam weighting CBW in addition to the normalized view-based motion map (vMMAP) weighting function.

For use in the fifth embodiment, the CBW+vMMAP weighting function $w_{CBW+vMMAP}(\beta,\gamma,v)$ is function of view angle $\beta$, fan angle $\gamma$ and vertical coordinate of the detector v and is normalized as defined below in Equation (24).

$$w_{CBW+vMMAP}(\beta, \gamma, v) = \frac{u_{CBW}(\beta, v)u_{vMMAP}(\beta)}{\sum_{n=-N_{PI}}^{N_{PI}} u_{CBW}(\beta_n^C, \gamma_n^C, v_n^C)u_{vMMAP}(\beta_n^C)} \quad (24)$$

In general, the normalized CBW+vMMAP weighting function $w_{CBW+vMMAP}(\beta,\gamma,v)$ is determined by normalizing CBW function $u_{CBW}(\beta,v)$ and vMMAP weighting function, $u_{vMMAP}(\beta)$ over a summation of $u_{CBW}(\beta_n^C,\gamma_n^C,v_n^C)$ and $u_{vMMAP}(\beta_n^C)$ from $n=-N_{PI}$ to $n=N_{PI}$ for complementary parameters $(\beta_n^C,\gamma_n^C,v_n^C)$.

For the definitions of the above functions, previously provided equations are referenced. For example, the normalized cone beam weighting CBW function $w_{CBW}(\beta,\gamma,v)$ is defined by Equation (20). The normalized view-based motion map vMMAP weighting function $w_{vMMAP}(\beta)$ is defined in Equation (6). One exemplary definition of the complementary view angles $(\beta_n^C)$ is defined by Equation (4) or (19A). One exemplary definition of the complementary detector coordinates $(v_n^C)$ is defined by the following Equation (19B). One exemplary definition of the complementary fan angle $(\gamma_n^C)$ is defined by the following Equation (9) or (19C). The value of $n=N_{PI}$ is determined to be as large as necessary to take into account all available cardiac data. The normalized CBW+vMMAP weighting function $w_{CBW+vMMAP}(\beta,\gamma,v)$ determines a weighting value ranging from 0 to 1 with respect to a particular view angle $\beta$, a particular fan angle $\gamma$ and a particular vertical coordinate v.

In the sixth embodiment, the processing unit or step performs tasks of additionally weighting the projection data that has been acquired during a helical trajectory of a cone beam source according to a ray-based motion map rMMAP. A cone beam weighting (CBW) technique is optionally extended to include rMMAP. As described above, the processing unit or step ultimately determines a weighting value according the normalized cone beam weighting CBW in addition to the normalized ray-based motion map (rMMAP) weighting function.

Figure 10:
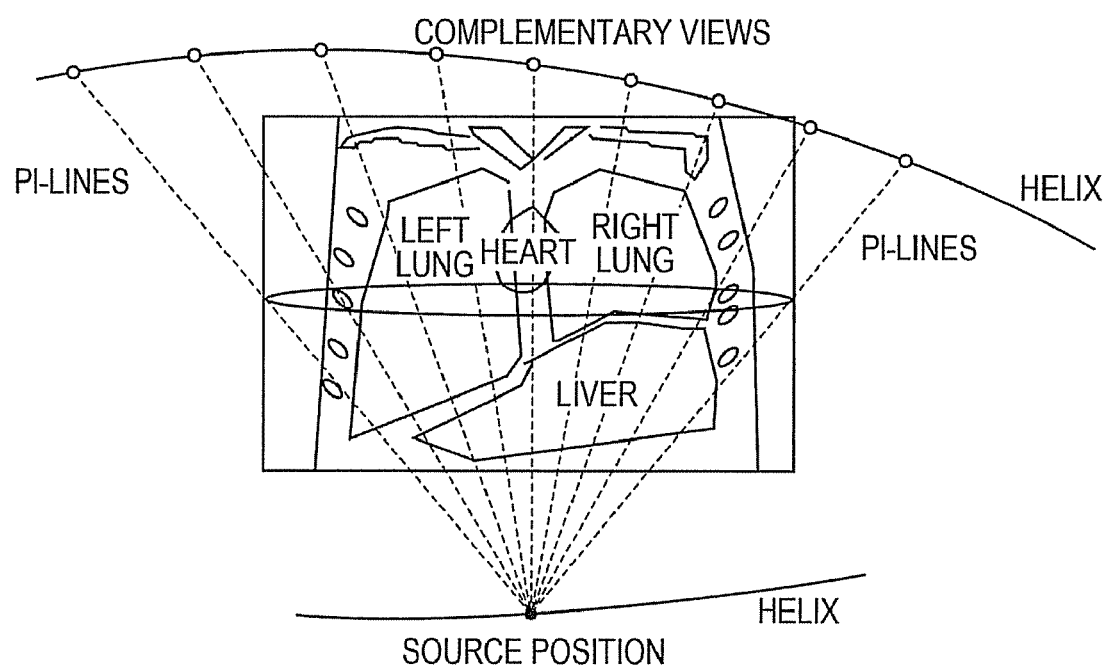
FIG. 10 is a diagram illustrating motion estimated using difference of measurements on PI-lines.

In general, FIG. 10 illustrates motion estimated using difference of measurements on PI-lines. At an arbitrary source position, complementary views are illustrated in dotted lines with respect to a predetermined helix where the source travels. The complementary views are also shown with respect to regions of interest such as moving heart and moving lungs.

For use in the sixth embodiment, the CBW+rMMAP weighting function $w_{CBW+rMMAP}(\beta,\gamma,v)$ is function of view angle $\beta$, fan angle $\gamma$ and vertical coordinate of the detector v and is normalized as defined below in Equation (25).

$$w_{CBW+rMMAP}(\beta, \gamma, v) = \frac{u_{CBW}(\beta, v)u_{rMMAP}(\beta, \gamma)}{\sum_{n=-N_{PI}}^{N_{PI}} u_{CBW}(\beta_n^C, \gamma_n^C, v_n^C)u_{rMMAP}(\beta_n^C, \gamma_n^C)} \quad (25)$$

In general, the normalized CBW+rMMAP weighting function $w_{CBW+rMMAP}(\beta,\gamma,v)$ is determined by normalizing CBW function $u_{CBW}(\beta,v)$ and rMMAP weighting function, $u_{rMMAP}(\beta,\gamma)$ over a summation of $u_{CBW}(\beta_n^C,\gamma_n^C,v_n^C)$ and $u_{rMMAP}(\beta_n^C,\gamma_n^C)$ from $n=-N_{PI}$ to $n=N_{PI}$ for complementary parameters $(\beta_n^C,\gamma_n^C,v_n^C)$.

For the definitions of the above functions, previously provided equations are referenced. For example, the normalized cone beam weighting CBW function $w_{CBW}(\beta,\gamma,v)$ is defined by Equation (20). The normalized ray-based motion map rMMAP weighting function $w_{rMMAP}(\beta,\gamma)$ is defined in Equation (8). One exemplary definition of the complementary view angles $(\beta_n^C)$ is defined by Equation (4) or (19A). One exemplary definition of the complementary detector coordinates $(v_n^C)$ is defined by the following Equation (19B). One exemplary definition of the complementary fan angle $(\gamma_n^C)$ is defined by the following Equation (9) or (19C). The value of $n=N_{PI}$ is determined to be as large as necessary to take into account all available cardiac data. The normalized CBW+rMMAP weighting function $w_{CBW+rMMAP}(\beta,\gamma,v)$ determines a weighting value ranging from 0 to 1 with respect to a particular view angle $\beta$, a particular fan angle $\gamma$ and a particular vertical coordinate v.

The above described combinations of the weighting functions is merely exemplary, and other embodiments of the current invention optionally weight the projection data based upon combinations other than the above described weighting functions. One such example is CBW+vMMAP+EGR weighting function and includes a combination of the cone beam weighting CBW function $u_{CBW}(\beta,v)$, view-based motion map vMMAP weighting function $u_{vMMAP}(\beta)$ and electrocardiogram gated reconstruction EGR weighting function $u_{EGR}(\phi(\beta))$. In this example, the combined weighting function is based upon two motion indexes such as view-based motion map and electrocardiogram gated reconstruction and a cone beam index.

The CBW+vMMAP+EGR weighting function is normalized and designated by $w_{CBW+vMMAP+EGR}(\beta,\gamma,v)$ as defined below in Equation (26).

$$w_{CBW+vMMAP+EGR}(\beta, \gamma, v) = \quad (26)$$

$$\frac{u_{CBW}(\beta, v)u_{vMMAP}(\beta)u_{EGR}(\varphi(\beta))}{\sum_{n=-N_{PI}}^{N_{PI}} u_{CBW}(\beta_n^C, \gamma_n^C, v_n^C)u_{vMMAP}(\beta_n^C)u_{EGR}(\varphi(\beta_n^C))}$$

In general, the normalized CBW+vMMAP+EGR weighting function $w_{CBW+vMMAP+EGR}(\beta,\gamma,v)$ is determined by normalizing CBW function $u_{CBW}(\beta,v)$, view-based motion map vMMAP weighting function $u_{vMMAP}(\beta)$ and EGR weighting function $u_{EGR}(\phi(\beta))$ over a summation of $u_{CBW}(\beta_n^C,\gamma_n^C,v_n^C)$, $u_{vMMAP}(\beta_n^C)$ and $u_{EGR}(\phi(\beta_n^C))$ from $n=-N_{PI}$ to $n=N_{PI}$ for complementary parameters $(\beta_n^C,\gamma_n^C,v_n^C)$.

For the definitions of the above functions, previously provided equations are referenced. For example, the normalized cone beam weighting CBW function $w_{CBW}(\beta,\gamma,v)$ is defined by Equation (20). The normalized view-based motion map vMMAP weighting function $w_{vMMAP}(\beta)$ is defined in Equation (6). One exemplary definition of the complementary view angles $(\beta_n^C)$ is defined by Equation (4) or (19A). One exemplary definition of the complementary detector coordinates $(v_n^C)$ is defined by the following Equation (19B). One exemplary definition of the complementary fan angle $(\gamma_n^C)$ is defined by the following Equation (9) or (19C). The value of $n=N_{PI}$ is determined to be as large as necessary to take into account all available cardiac data. The normalized CBW+vMMAP+EGR weighting function $w_{CBW+vMMAP+EGR}(\beta,\gamma,v)$ determines a weighting value ranging from 0 to 1 with respect to a particular view angle $\beta$, a particular fan angle $\gamma$ and a particular vertical coordinate $v$.

In another example, a CBW+rMMAP+EGR weighting function includes a combination of the cone beam weighting CBW function $u_{CBW}(\beta,v)$, ray-based motion map rMMAP weighting function $u_{rMMAP}(\beta,\gamma)$ and electrocardiogram gated reconstruction EGR weighting function $u_{EGR}(\phi(\beta))$. In this example, the combined weighting function is based upon two motion indexes such as rau-based motion map and electrocardiogram gated reconstruction and a fan beam index.

The CBW+rMMAP+EGR weighting function is normalized and designated by $w_{CBW+rMMAP+EGR}(\beta,\gamma,v)$ as defined below in Equation (27).

$$w_{CBW+rMMAP+EGR}(\beta, \gamma, v) = \quad (27)$$

$$\frac{u_{CBW}(\beta, v)u_{rMMAP}(\beta, \gamma)u_{EGR}(\varphi(\beta))}{\sum_{n=-N_{PI}}^{N_{PI}} u_{CBW}(\beta_n^C, \gamma_n^C, v_n^C)u_{rMMAP}(\beta_n^C, \gamma_n^C)u_{EGR}(\varphi(\beta_n^C))}$$

In general, the normalized CBW+rMMAP+EGR weighting function $w_{CBW+rMMAP+EGR}(\beta,\gamma,v)$ is determined by normalizing CBW function $u_{CBW}(\beta,v)$, ray-based motion map rMMAP weighting function $u_{rMMAP}(\beta,\gamma)$ and EGR weighting function $u_{EGR}(\phi(\beta))$ over a summation of $u_{CBW}(\beta_n^C,\gamma_n^C,v_n^C)$, $u_{rMMAP}(\beta_n^C,\gamma_n^C)$ and $u_{EGR}(\phi(\beta_n^C))$ from $n=-N_{PI}$ to $n=N_{PI}$ for complementary view and fan angles $(\beta_n^C,\gamma_n^C)$.

For the definitions of the above functions, previously provided equations are referenced. For example, the normalized cone beam weighting CBW function $w_{CBW}(\beta,\gamma,v)$ is defined by Equation (20). The normalized ray-based motion map rMMAP weighting function $u_{rMMAP}(\beta,\gamma)$ is defined in Equation (8). One exemplary definition of the complementary view angles $(\beta_n^C)$ is defined by Equation (4) or (19A). One exemplary definition of the complementary detector coordinates $(v_n^C)$ is defined by the following Equation (19B). One exemplary definition of the complementary fan angle $(\gamma_n^C)$ is defined by the following Equation (9) or (19C). The normalized FB+rMMAP+EGR weighting function $w_{CBW+rMMAP+EGR}(\beta,\gamma,v)$ determines a weighting value ranging from 0 to 1 with respect to a particular view angle $\beta$ and a particular fan angle $\gamma$.

Figures 11A, 11B, 11C:
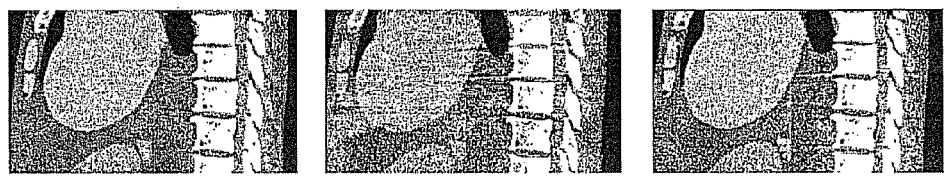
FIG. 11A illustrates a wide cone angle helical reconstruction of a motionless phantom.
FIG. 11B illustrates a standard helical ECG-gated segmented reconstruction with assumed motion.
FIG. 11C illustrates a reconstruction example using some of the above described embodiments based upon the same motion of FIG. 11B.

FIGS. 11A, 11B and 11C show some effects of the above described weighting according to the current invention. FIG. 11A illustrates a wide cone angle helical reconstruction of a motionless phantom. FIG. 11B illustrates a standard helical ECG-gated segmented reconstruction with assumed motion. Artifacts as seen in FIG. 11B are caused primarily by the cone angle rather than by motion. FIG. 11C illustrates a reconstruction example using some of the above described embodiments based upon the same motion of FIG. 11B.

Figures 12A, 12B:
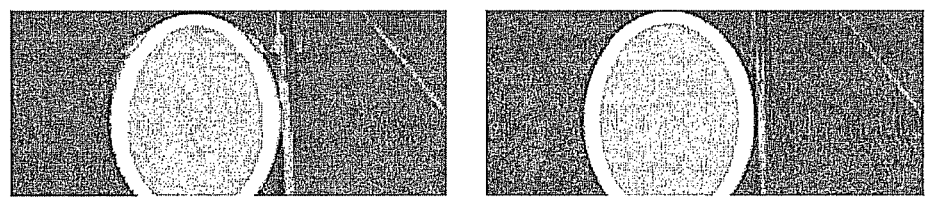
FIG. 12A illustrates a standard helical ECG-gated segmented reconstruction.
FIG. 12B illustrates a helical ECG-gated segmented reconstruction using some of the above described embodiments.

FIGS. 12A and 12B illustrate computer simulated cardiac motion phantom with fast heart beat. Projection data is collected with wide cone angle. FIG. 12A illustrates a standard helical ECG-gated segmented reconstruction. FIG. 12B illustrates a helical ECG-gated segmented reconstruction using some of the above described embodiments.

Some of the above described embodiments improve cone beam shading in helical ECG-gated reconstruction as well as transition between ECG patches due to the smooth weighting. Furthermore, because of efficient data utilization, the above described embodiments optionally increase the helical pitch in ECG-gated data collection and consequently result in faster scans with a lower dose than prior art.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope of the inventions.

What is claimed is:

1. A method of weighting projection data in a computed tomography (CT) system, comprising the steps of:
   acquiring projection data using a cone beam along a circular trajectory in the CT system;
   determining a weight value according to a normalized electrocardiogram gated reconstruction (EGR) weighting function, $w_{EGR}(\beta,\gamma)$ based upon an EGR weighting function $u_{EGR}(\phi(\beta))$ at a cardiac phase $\phi$ and a view angle $\beta$, said $u_{EGR}(\phi(\beta))$ being normalized by a summation of $u_{EGR}(\phi(\beta_n^C))$ from $n=-N_{PI}$ to $n=N_{PI}$ for complementary view angles $(\beta_n^C)$ during the cardiac phase $\phi$, wherein said determining step determines said weight value according to a FB+EGR weighting function $w_{FB+EGR}(\beta,\gamma)$ based upon said $u_{EGR}(\phi(\beta))$ and a fan beam (FB) weighting function $u_{FB}(\beta)$ at the view angle $\beta$, a product of said $u_{EGR}(\phi(\beta))$ and said $u_{FB}(\beta)$ being normalized by the summation of a product of $u_{FB}(\beta_n^C,\gamma_n^C)$ and $u_{EGR}(\phi(\beta_n^C))$ from $n=-N_{PI}$ to $n=N_{PI}$ for the complementary view angles $(\alpha_n^C)$ and complementary fan angles $(\gamma_n^C)$; and
   weighting each of the projection data by said weight value as determined by said $w_{EGR}(\beta,\gamma)$ for the CT system, where $\gamma$ is a fan angle of the cone beam.

2. The method of weighting projection data according to claim 1 wherein said $u_{EGR}(\phi(\beta))$ is defined as $$\exp\left(-\frac{(\varphi(\beta)-\varphi_0)^2}{\sigma_{EGR}^2}\right),$$

where a slice is reconstructed at a phase $\phi_0$ while $\sigma_{EGR}$ is a predetermined empirical parameter.

3. The method of weighting projection data according to claim 1 wherein said $u_{FB}(\beta)$ is defined as:

$$u_{FB}(\beta) = \begin{cases} 0, & \beta < \beta_{start} \\ p\left(\frac{\beta - \beta_{start}}{\Delta\beta}\right), & \beta_{start} \leq \beta < \beta_{start} + \Delta\beta \\ 1, & \beta_{start} + \Delta\beta \leq \beta \leq \beta_{end} - \Delta\beta \\ p\left(\frac{\beta_{end} - \beta}{\Delta\beta}\right), & \beta_{end} - \Delta\beta < \beta \leq \beta_{end} \\ 0, & \beta > \beta_{end} \end{cases}$$

where $\Delta\beta$ is a predetermined smoothing interval, $\beta_{start}$ and $\beta_{end}$ are respectively a start and an end of an image reconstruction view range.

4. The method of weighting projection data according to claim 3 wherein said function $p(\ )$ includes $$p(x) = x,\ p(x) = 3x^2 - 2x^3,\ p(x) = \frac{1}{2}(1 - \cos(\pi x))\ \text{and}$$

$$p(x) = \sin^2\left(\frac{\pi x}{2}\right).$$

5. The method of weighting projection data according to claim 1 wherein said determining step determines said weight value according to a FB+EGR+vMMAP weighting function $w_{FB+EGR+vMMAP}(\beta,\gamma)$ based upon said $u_{EGR}(\phi(\beta))$ said $u_{FB}(\beta)$ and a view-based motion map (vMMAP) weighting function $u_{vMMAP}(\beta)$ at the view angle $\beta$, a product of said $u_{EGR}(\phi(\beta))$, said $u_{FB}(\beta, v)$ and said $u_{vMMAP}(\beta)$ being normalized by the summation of a product of said $u_{FB}(\beta_n^C,\gamma_n^C)$, said $u_{EGR}(\phi(\beta_n^C))$ and a $u_{vMMAP}(\beta_n^C)$ from $n=-N_{PI}$ to $n=N_{PI}$ or the complementary view angles $(\beta_n^C)$ and the complementary fan angles $(\gamma_n^C)$.

6. The method of weighting projection data according to claim 5 wherein said $u_{vMMAP}(\beta)$ is defined as $$p\left(\frac{maxMmap - MMAP(\beta)}{maxMmap - minMmap}\right),$$

where $$vMMAP(\beta) = \sum_{ch} abs(diff[ch, \beta]),$$

ch is a channel, $maxMmap=max(MMAP(\beta))$, $minMmap=min(MMAP(\beta))$, $p(\ )$ is generally a function that satisfies the following conditions: $p(0)=0$, $p(1)=1$, and $p(x)$ also monotonically increases from 0 to 1 as the variable x increases.

7. The method of weighting projection data according to claim 1 wherein said weighting step takes place before back-projection.

8. A method of weighting projection data in a computed tomography (CT) system, comprising the steps of:
    acquiring projection data using a cone beam along a circular trajectory in the CT system;
    determining a weight value according to a normalized view-based motion map (vMMAP) weighting function $w_{vMMAP}(\beta,\gamma)$ at a view angle $\beta$, a vMMAP weighting function $u_{vMMAP}(\beta)$ being normalized by a summation of $u_{vMMAP}(\beta_n^C)$ from $n=-N_{PI}$ to $n=N_{PI}$ for complementary view angles $(\beta_n^C)$, wherein said determining step determines said weight value according to a FB+vMMAP weighting function $w_{FB+vMMAP}(\beta,\gamma)$ based upon said $u_{vMMAP}(\beta)$ and a fan beam (FB) weighting function $u_{FB}(\beta)$ at the view angle $\beta$, a product of said $u_{vMMAP}(\beta)$ and said $u_{FB}(\beta)$ being normalized by the summation of a product of $u_{FB}(\beta_n^C,\gamma_n^C)$ and $u_{vMMAP}(\beta_n^C)$ from $n=-N_{PI}$ to $n=N_{PI}$ for the complementary view angles $(\beta_n^C)$ and complementary fan angles $(\gamma_n^C)$; and
    weighting each of the projection data by said weight value as determined by said $w_{vMMAP}(\beta,\gamma)$ for the CT system, where $\gamma$ is a fan angle of the cone beam.

9. The method of weighting projection data according to claim 8 wherein said $u_{vMMAP}(\beta)$ is defined as $$p\left(\frac{maxMmap - MMAP(\beta)}{maxMmap - minMmap}\right),$$

where $$vMMAP(\beta) = \sum_{ch} abs(diff[ch, \beta]),$$

ch is a channel, $maxMmap=max(MMAP(\beta))$, $minMmap=min(MMAP(\beta))$, $p(\ )$ is generally a function that satisfies the following conditions: $p(0)=0$, $p(1)=1$, and $p(x)$ also monotonically increases from 0 to 1 as the variable x increases.

10. The method of weighting projection data according to claim 8 wherein said $u_{FB}(\beta)$ is defined as:

$$u_{FB}(\beta) = \begin{cases} 0, & \beta < \beta_{start} \\ p\left(\frac{\beta - \beta_{start}}{\Delta\beta}\right), & \beta_{start} \leq \beta < \beta_{start} + \Delta\beta \\ 1, & \beta_{start} + \Delta\beta \leq \beta \leq \beta_{end} - \Delta\beta \\ p\left(\frac{\beta_{end} - \beta}{\Delta\beta}\right), & \beta_{end} - \Delta\beta < \beta \leq \beta_{end} \\ 0, & \beta > \beta_{end} \end{cases}$$

where $\Delta\beta$ is a predetermined smoothing interval, $\beta_{start}$ and $\beta_{end}$ are respectively a start and an end of an image reconstruction view range.

11. The method of weighting projection data according to claim 10 wherein said function $p(\ )$ includes $$p(x) = x,\ p(x) = 3x^2 - 2x^3,\ p(x) = \frac{1}{2}(1 - \cos(\pi x))\ \text{and}$$

$$p(x) = \sin^2\left(\frac{\pi x}{2}\right).$$

12. The method of weighting projection data according to claim 8 wherein said weighting step takes place before back-projection.

13. A method of weighting projection data in a computed tomography (CT) system, comprising the steps of:
acquiring projection data using a cone beam along a circular trajectory in the CT system;
determining a weight value according to a normalized ray-based motion map (rMMAP) weighting function $w_{rMMAP}(\beta,\gamma)$ at a view angle $\beta$ and a fan angle $\gamma$, a rMMAP weighting function $u_{rMMAP}(\beta,\gamma)$ being normalized by a summation of $u_{rMMAP}(\beta_n^C,\gamma_n^C)$ from $n=-N_{PI}$ to $n=N_{PI}$ for complementary view and fan angles $(\beta_n^C, \gamma_n^C)$; and
weighting each of the projection data by said weight value as determined by said $w_{rMMAP}(\beta,\gamma)$ for the CT system.

14. The method of weighting projection data according to claim 13 wherein said $u_{rMMAP}(\beta,\gamma)$ is assigned a weight value of 1 if a view is the closest to an image plane, while other views are each assigned a value that is determined by an amount of motion between two complementary rays AB and BA, the amount of motion being defined by $m(AB)=f(|g(BA)-g(AB)|)$, where $g(.)$ is measured raw while $f(.)$ is a predetermined function such that $f(0)=1$ and $f(t) \to 0$ as t increases.

15. The method of weighting projection data according to claim 13 wherein said determining step determines said weight value according to a FB+rMMAP weighting function $w_{FB+rMMAP}(\beta,\gamma)$ based upon said $u_{rMMAP}(\beta,\gamma)$ and a fan beam (FB) weighting function $u_{FB}(\beta)$, a product of said $u_{rMMAP}(\beta,\gamma)$ and said $u_{FB}(\beta)$ being normalized by the summation of a product of $u_{FB}(\beta_n^C,\gamma_n^C)$ and $u_{rMMAP}(\gamma_n^C,\gamma_n^C)$ from $n=-N_{PI}$ to $n=N_{PI}$ for the complementary view angles $(\beta_n^C)$ and complementary fan angles $(\gamma_n^C)$.

16. The method of weighting projection data according to claim 15 wherein said $u_{FB}(\beta)$ is defined as:

$$u_{FB}(\beta) = \begin{cases} 0, & \beta < \beta_{start} \\ p\left(\dfrac{\beta - \beta_{start}}{\Delta\beta}\right), & \beta_{start} \le \beta < \beta_{start} + \Delta\beta \\ 1, & \beta_{start} + \Delta\beta \le \beta \le \beta_{end} - \Delta\beta \\ p\left(\dfrac{\beta_{end} - \beta}{\Delta\beta}\right), & \beta_{end} - \Delta\beta < \beta \le \beta_{end} \\ 0, & \beta > \beta_{end} \end{cases}$$

where $\Delta\beta$ is a predetermined smoothing interval, $\beta_{start}$ and $\beta_{end}$ are respectively a start and an end of an image reconstruction view range.

17. The method of weighting projection data according to claim 16 wherein said function $p(\ )$ includes $$p(x) = x, \quad p(x) = 3x^2 - 2x^3, \quad p(x) = \frac{1}{2}(1-\cos(\pi x)) \text{ and}$$
$$p(x) = \sin^2\left(\frac{\pi x}{2}\right).$$

18. The method of weighting projection data according to claim 15 wherein said determining step determines said weight value according to a FB+EGR+rMMAP weighting function $w_{FB+EGR+rMMAP}(\beta,\gamma)$ based upon an electrocardiogram gated reconstruction (EGR) $u_{EGR}(\phi(\beta))$, said $u_{FB}(\beta)$ and said $u_{rMMAP}(\beta,\gamma)$, a product of said $u_{FB}(\beta,v)$, said $u_{EGR}(\phi(\beta))$ and said $u_{rMMAP}(\beta,\gamma)$ being normalized by a summation of a product of said $u_{FB}(\beta_n^C,\gamma_n^C)$, said $u_{rMMAP}(\beta_n^C,\gamma_n^C)$ and a $u_{EGR}(\phi(\beta_n^C))$ from $n=-N_{PI}$ to $n=N_{PI}$ for the complementary view angles $(\beta_n^C)$ and the complementary fan angles $(\gamma_n^C)$.

19. The method of weighting projection data according to claim 13 wherein said weighting step takes place before back-projection.

20. A method of weighting projection data in a computed tomography (CT) system, comprising the steps of:
acquiring projection data using a cone beam along a helical trajectory in the CT system;
determining a weight value according to a normalized cone beam and electrocardiogram gated reconstruction (CBW+EGR) weighting function $w_{CBW+EGR}(\beta,\gamma,v)$ based upon an EGR weighting function $u_{EGR}(\phi(\beta))$ and a cone beam weighting function, $u_{CBW}(\beta,v)$ at a view angle $\beta$, a cardiac phase $\phi$, a fan angle $\gamma$ and a vertical coordinate $v$, said $u_{EGR}(\phi(\beta))$ and said $u_{CBW}(\beta,v)$ being normalized by a summation of $u_{EGR}(\phi(\beta_n^C))$ and $u_{CBW}(\beta_n^C,\gamma_n^C,v_n^C)$ from $n=-N_{PI}$ to $n=N_{PI}$ for complementary view and fan angles and complementary vertical coordinate $(\beta_n^C,\gamma_n^C,v_n^C)$, wherein said $u_{CBW}(\beta, v)$ is defined by a product of $u_{FB}(\beta,\gamma)$ and $u_{CB}(v)$ where said $u_{FB}$ is a fan beam; and
weighting each of the projection data by said weight value as determined by said $w_{CBW+EGR}(\beta,\gamma,v)$ for the CT system.

21. The method of weighting projection data according to claim 20 wherein said $u_{EGR}(\phi(\beta))$ is defined as $$\exp\left(-\frac{(\varphi(\beta)-\varphi_0)^2}{\sigma_{EGR}^2}\right),$$

where a slice is reconstructed at a phase $\phi_0$ while $\sigma_{EGR}$ is a predetermined empirical parameter.

22. The method of weighting projection data according to claim 20 wherein said $u_{FB}(\beta)$ is defined as:

$$u_{FB}(\beta) = \begin{cases} 0, & \beta < \beta_{start} \\ p\left(\dfrac{\beta - \beta_{start}}{\Delta\beta}\right), & \beta_{start} \le \beta < \beta_{start} + \Delta\beta \\ 1, & \beta_{start} + \Delta\beta \le \beta \le \beta_{end} - \Delta\beta \\ p\left(\dfrac{\beta_{end} - \beta}{\Delta\beta}\right), & \beta_{end} - \Delta\beta < \beta \le \beta_{end} \\ 0, & \beta > \beta_{end} \end{cases}$$

where $\Delta\beta$ is a predetermined smoothing interval, $\beta_{start}$ and $\beta_{end}$ are respectively a start and an end of an image reconstruction view range.

23. The method of weighting projection data according to claim 20 wherein said function $p(\ )$ includes $$p(x) = x, \quad p(x) = 3x^2 - 2x^3, \quad p(x) = \frac{1}{2}(1-\cos(\pi x)) \text{ and}$$
$$p(x) = \sin^2\left(\frac{\pi x}{2}\right).$$

24. The method of weighting projection data according to claim 20 wherein said $u_{CB}(v)$, is defined as:

$$u_{CB}(v) = \begin{cases} 0, & v \leq -W \\ p\left(\frac{W+v}{\Delta v}\right), & -W < v < -W + \Delta v \\ 1, & -W + \Delta v \leq v \leq W - \Delta v \\ p\left(\frac{W-v}{\Delta v}\right) & W - \Delta v < v < W \\ 0, & v \geq W \end{cases}$$

Where the function p( ) includes $$p(x) = x, \ p(x) = 3x^2 - 2x^3, \ p(x) = \frac{1}{2}(1 - \cos(\pi x)) \text{ and}$$

$$p(x) = \sin^2\left(\frac{\pi x}{2}\right).$$

25. The method of weighting projection data according to claim 20 wherein said determining step determines said weight value according to a CBW+EGR+vMMAP weighting function $w_{CBW+vMMAP+EGR}(\beta,\gamma,v)$ based upon said $u_{EGR}(\phi(\beta))$, said $u_{CBW}(\beta,v)$ and a view-based motion map (vMMAP) weighting function $u_{vMMAP}(\beta)$ at the view angle $\beta$, a product of said $u_{EGR}(\phi(\beta))$, said $u_{CBW}(\beta,v)$ and said $u_{vMMAP}(\beta)$ being normalized by the summation of a product of said $u_{CBW}(\beta_n{}^C, \gamma_n{}^C, v_n{}^C)$, said $u_{EGR}(\phi(\beta_n{}^C))$ and said $u_{vMMAP}(\beta_n{}^C)$ from $n=-N_{PI}$ to $n=N_{PI}$ for the complementary view and fan angles and the complementary vertical coordinate $(\beta_n{}^C, \gamma_n{}^C, v_n{}^C)$.

26. The method of weighting projection data according to claim 25 wherein said $u_{vMMAP}(\beta)$ is defined as $$p\left(\frac{maxMmap - MMAP(\beta)}{maxMmap - minMmap}\right),$$

where $$vMMAP(\beta) = \sum_{ch} abs(diff[ch, \beta]),$$

ch is a channel, maxMmap=max(MMAP($\beta$)), minMmap=min(MMAP($\beta$)), p( ) is generally a function that satisfies the following conditions: p(0)=0, p(1)=1, and p(x) also monotonically increases from 0 to 1 as the variable x increases.

27. The method of weighting projection data according to claim 20 wherein said weighting-step takes place before backprojection.

28. A method of weighting projection data in a computed tomography (CT) system, comprising the steps of:
acquiring projection data using a cone beam along a helical trajectory in the CT system;
determining a weight value according to a normalized cone beam and view-based motion map (CBW+vMMAP) weighting function $w_{CBW+vMMAP}(\beta,\gamma,v)$ based upon a vMMAP weighting function $u_{vMMAP}(\beta)$ and a cone beam weighting function $u_{CBW}(\beta,v)$ at a view angle $\beta$, a fan angle $\gamma$ and a vertical coordinate v, said $u_{vMMAP}(\beta)$ and said $u_{CBW}(\beta,v)$ being normalized by a summation of $u_{vMMAP}(\beta_n{}^C)$ and $u_{CBW}(\beta_n{}^C,\gamma_n{}^C,v_n{}^C)$ from $n=-N_{PI}$ to $n=N_{PI}$ for complementary view and fan angles and complementary vertical coordinate $(\beta_n{}^C,\gamma_n{}^C,v_n{}^C)$, wherein said $u_{CBW}(\beta,v)$ is defined by a product of $u_{FB}(\beta,\gamma)$ and $u_{CB}(v)$ where said $u_{FB}$ is a fan beam; and
weighting each of the projection data by said weight value as determined by said $w_{CBW+vMMAP}(\beta,\gamma,v)$ for the CT system.

29. The method of weighting projection data according to claim 28 wherein said $u_{FB}(\beta)$ is defined as:

$$u_{FB}(\beta) = \begin{cases} 0, & \beta < \beta_{start} \\ p\left(\frac{\beta - \beta_{start}}{\Delta \beta}\right), & \beta_{start} \leq \beta < \beta_{start} + \Delta \beta \\ 1, & \beta_{start} + \Delta \beta \leq \beta \leq \beta_{end} - \Delta \beta \\ p\left(\frac{\beta_{end} - \beta}{\Delta \beta}\right) & \beta_{end} - \Delta \beta < \beta \leq \beta_{end} \\ 0, & \beta > \beta_{end} \end{cases}$$

where $\Delta\beta$ is a predetermined smoothing interval, $\beta_{start}$ and $\beta_{end}$ are respectively a start and an end of an image reconstruction view range.

30. The method of weighting projection data according to claim 29 wherein said function p( ) includes $$p(x) = x, \ p(x) = 3x^2 - 2x^3, \ p(x) = \frac{1}{2}(1 - \cos(\pi x)) \text{ and}$$

$$p(x) = \sin^2\left(\frac{\pi x}{2}\right).$$

31. The method of weighting projection data according to claim 28 wherein said $u_{CB}(v)$ is defined as:

$$u_{CB}(v) = \begin{cases} 0, & v \leq -W \\ p\left(\frac{W+v}{\Delta v}\right), & -W < v < -W + \Delta v \\ 1, & -W + \Delta v \leq v \leq W - \Delta v \\ p\left(\frac{W-v}{\Delta v}\right) & W - \Delta v < v < W \\ 0, & v \geq W \end{cases}$$

where the function p( ) includes $$p(x) = x, \ p(x) = 3x^2 - 2x^3, \ p(x) = \frac{1}{2}(1 - \cos(\pi x)) \text{ and}$$

$$p(x) = \sin^2\left(\frac{\pi x}{2}\right).$$

32. The method of weighting projection data according to claim 28 wherein said $u_{vMMAP}(\beta)$ is defined as $$p\left(\frac{maxMmap - MMAP(\beta)}{maxMmap - minMmap}\right),$$

where $$vMMAP(\beta) = \sum_{ch} abs(diff[ch, \beta]),$$

ch is a channel, maxMmap=max(MMAP(β)), minMmap=min(MMAP(β)), p( ) is generally a function that satisfies the following conditions: p(0)=0, p(1)=1, and p(x) also monotonically increases from 0 to 1 as the variable x increases.

33. The method of weighting projection data according to claim 28 wherein said weighting step takes place before back-projection.

34. A method of weighting projection data in a computed tomography (CT) system, comprising the steps of:
  acquiring projection data using a cone beam along a helical trajectory in the CT system;
  determining a weight value according to a normalized cone beam and ray-based motion map (CBW+rMMAP) weighting function $w_{CBW+rMMAP}(\beta,\gamma,v)$ based upon a rMMAP weighting function $u_{rMMAP}(\beta,\gamma)$ and a cone beam weighting function $u_{CBW}(\beta,v)$ at a view angle β, a fan angle γ and a vertical coordinate v, said $u_{rMMAP}(\beta,\gamma)$ and said $u_{CBW}(\beta,v)$ being normalized by a summation of $u_{rMMAP}(\beta_n^C,\gamma_n^C)$ and $u_{CBW}(\beta_n^C,\gamma_n^C,v_n^C)$ from n=−$N_{PI}$ to n=$N_{PI}$ for complementary view and fan angles and complementary vertical coordinate ($\beta_n^C,\gamma_n^C,v_n^C$), wherein said $u_{CBW}(\beta,v)$ is defined by a product of $u_{FB}(\beta,\gamma)$ and $u_{CB}(v)$ where said $u_{FB}$ is a fan beam; and
  weighting each of the projection data by said weight value as determined by said $w_{CBW+rMMAP}(\beta,\gamma,v)$ for the CT system.

35. The method of weighting projection data according to claim 34 wherein said $u_{FB}(\beta)$ is defined as:

$$u_{FB}(\beta) = \begin{cases} 0, & \beta < \beta_{start} \\ p\left(\frac{\beta - \beta_{start}}{\Delta\beta}\right), & \beta_{start} \leq \beta < \beta_{start} + \Delta\beta \\ 1, & \beta_{start} + \Delta\beta \leq \beta \leq \beta_{end} - \Delta\beta \\ p\left(\frac{\beta_{end} - \beta}{\Delta\beta}\right) & \beta_{end} - \Delta\beta < \beta \leq \beta_{end} \\ 0, & \beta > \beta_{end} \end{cases}$$

where Δβ is a predetermined smoothing interval, $\beta_{start}$ and $\beta_{end}$ are respectively a start and an end of an image reconstruction view range.

36. The method of weighting projection data according to claim 35 wherein said function p( ) includes $$p(x) = x, \; p(x) = 3x^2 - 2x^3, \; p(x) = \frac{1}{2}(1 - \cos(\pi x)) \text{ and}$$

$$p(x) = \sin^2\left(\frac{\pi x}{2}\right).$$

37. The method of weighting projection data according to claim 34 wherein said $u_{CB}(v)$, is defined as:

$$u_{CB}(v) = \begin{cases} 0, & v \leq -W \\ p\left(\frac{W+v}{\Delta v}\right), & -W < v < -W + \Delta v \\ 1, & -W + \Delta v \leq v \leq W - \Delta v \\ p\left(\frac{W-v}{\Delta v}\right) & W - \Delta v < v < W \\ 0, & v \geq W \end{cases}$$

where the function p( ) includes $$p(x) = x, \; p(x) = 3x^2 - 2x^3, \; p(x) = \frac{1}{2}(1 - \cos(\pi x)) \text{ and}$$

$$p(x) = \sin^2\left(\frac{\pi x}{2}\right).$$

38. The method of weighting projection data according to claim 34 wherein said $u_{rMMAP}(\beta,\gamma)$ is assigned a weight value of 1 if a view is the closest to an image plane, while other views are each assigned a value that is determined by an amount of motion between two complementary rays AB and BA, the amount of motion being defined by m(AB)=f(|g(BA)−g(AB)|), where g(.) is measured raw while f(.) is a predetermined function such that f(0)=1 and f(t)→0 as t increases.

39. The method of weighting projection data according to claim 34 wherein said determining step determines said weight value according to a CBW+EGR+rMMAP weighting function $w_{CBW+EGR+rMMAP}(\beta,\gamma,v)$ based upon an electrocardiogram gated reconstruction (EGR) $u_{EGR}(\phi(\beta))$, said $u_{CBW}(\beta,v)$ and said $u_{rMMAP}(\beta,\gamma)$, a product of said $u_{CBW}(\beta,v)$, said $u_{EGR}(\phi(\beta))$ and said $u_{CBW}(\beta,\gamma)$ being normalized by a summation of a product of said $u_{CBW}(\beta_n^C,\gamma_n^C,v_n^C)$, said $u_{rMMAP}(\beta_n^C,\gamma_n^C)$, and a $u_{EGR}(\phi(\beta_n^C))$ from n=−$N_{PI}$ to n=$N_{PI}$ for the complementary view and fan angles and the complementary vertical coordinate ($\beta_n^C,\gamma_n^C,v_n^C$).

40. The method of weighting projection data according to claim 34 wherein said weighting step takes place before back-projection.

* * * * *